US012534455B2

(12) United States Patent
Fiorelli et al.

(10) Patent No.: US 12,534,455 B2
(45) Date of Patent: Jan. 27, 2026

(54) PHTHALAZINE DERIVATIVES AS P2X$_3$ INHIBITORS

(71) Applicant: CHIESI FARMACEUTICI S.P.A., Parma (IT)

(72) Inventors: Claudio Fiorelli, Parma (IT); Paolo Bruno, Parma (IT); Matteo Biagetti, Parma (IT); Charles Baker-Glenn, Parma (IT); Hervè Van De Poöel, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 447 days.

(21) Appl. No.: 18/038,802

(22) PCT Filed: Nov. 26, 2021

(86) PCT No.: PCT/EP2021/083146

§ 371 (c)(1),
(2) Date: May 25, 2023

(87) PCT Pub. No.: WO2022/112493

PCT Pub. Date: Jun. 2, 2022

(65) Prior Publication Data

US 2024/0002371 A1 Jan. 4, 2024

(30) Foreign Application Priority Data

Nov. 27, 2020 (EP) .................................... 20210200

(51) Int. Cl.

| | |
|---|---|
| ***C07D 405/14*** | (2006.01) |
| ***C07D 237/34*** | (2006.01) |
| ***C07D 403/12*** | (2006.01) |
| ***C07D 417/14*** | (2006.01) |

(52) U.S. Cl.
CPC ......... *C07D 405/14* (2013.01); *C07D 237/34* (2013.01); *C07D 403/12* (2013.01); *C07D 417/14* (2013.01)

(58) Field of Classification Search
CPC .. C07D 405/14; C07D 237/34; C07D 403/12; C07D 417/14; C07D 237/30; C07D 401/14; C07D 403/14; A61P 11/00; A61P 11/14; A61K 31/502; A61K 31/506
See application file for complete search history.

(56) References Cited

U.S. PATENT DOCUMENTS

2011/0009432 A1 1/2011 Wei et al.

FOREIGN PATENT DOCUMENTS

| | | | | |
|---|---|---|---|---|
| JP | WO9942452 | * | 8/1990 | ........... C07D 237/34 |
| WO | WO-2018064135 A1 | | 4/2018 | |
| WO | WO-2021127429 A1 | | 6/2021 | |

OTHER PUBLICATIONS

International Search Report and Written Opinion issued Feb. 1, 2022 in PCT/EP2021/083146.

* cited by examiner

*Primary Examiner* — Joseph K Mckane
*Assistant Examiner* — David M Shim
(74) *Attorney, Agent, or Firm* — Element IP, PLC

(57) ABSTRACT

The present invention relates to compounds of formula (I) inhibiting P2X purinoceptor 3; particularly the invention relates to compounds that are phthalazine derivatives, methods of preparing such compounds, pharmaceutical compositions containing them and therapeutic use thereof. The compounds of the invention may be useful in the treatment of many disorders associated with P2X$_3$ receptors mechanisms, such as respiratory diseases including cough, asthma, idiopathic pulmonary fibrosis (IPF) and chronic obstructive pulmonary disease (COPD).

9 Claims, No Drawings

PHTHALAZINE DERIVATIVES AS $P2X_3$ INHIBITORS

FIELD OF THE INVENTION

The present invention relates to compounds inhibiting P2X purinoceptor 3 (hereinafter $P2X_3$ inhibitors); particularly the invention relates to compounds that are phthalazine derivatives, methods of preparing such compounds, pharmaceutical compositions containing them and therapeutic use thereof.

The compounds of the invention may be useful in the treatment of many disorders associated with $P2X_3$ receptors mechanisms, such as respiratory diseases including cough, asthma, idiopathic pulmonary fibrosis (IPF) and chronic obstructive pulmonary disease (COPD).

BACKGROUND OF THE INVENTION

P2X receptors are cell surface ion channels activated by extracellular Adenosine 5-TriPhosphate (ATP). P2X receptor family are trimeric assemblies composed of seven distinct subunit subtypes (P2X1-7) that assemble as homomeric and heteromeric channels. All subunits share a common topology containing intracellular termini, two transmembrane helices forming the ion channels and a large extracellular domain containing the ATP binding site. Homomeric $P2X_1$, $P2X_2$, $P2X_3$, $P2X_4$, $P2X_5$, and $P2X_7$ channels and heteromeric $P2X_{2/3}$ and $P2X_{1/5}$ channels have been fully characterized following heterologous expression. P2X receptors are abundantly distributed, and functional responses are seen in neurons, glia, epithelia, endothelia, bone, muscle, and hemopoietic tissues. On smooth muscles, P2X receptors respond to ATP released from sympathetic motor nerves (e.g., in ejaculation). On sensory nerves, they are involved in the initiation of afferent signals in several viscera (e.g., bladder, intestine) and play a key role in sensing tissue-damaging and inflammatory stimuli. Paracrine roles for ATP signaling through P2X receptors are likely in neurohypophysis, ducted glands, airway epithelia, kidney, bone and hemopoietic tissues. (RA. North: Molecular Physiology of P2X Receptors; Physiol Rev, Vol 82, October 2002). All P2X receptors are non-selective cation channels permeable to Na+ and Ca+ ions and are activated by ATP; however, the pharmacology of the receptor subtypes varies with respect to sensitivity to ATP and to small molecules antagonists. (K Kaczmarek-Hajek et al: Molecular and functional properties of P2X receptors—recent progress and persisting challenges; Purinergic Signalling 8:375-417, 2012)

In humans, the $P2X_3$ receptor has been reported in heart and spinal cord at the mRNA level and in DRG, intestine (myenteric plexus neurons), urinary bladder (urothelium and suburothelium), and dental pulp at the protein level (Garcia-Guzman M et al: Molecular characterization and pharmacological properties of the human $P2X_3$ purinoceptor: Brain Res Mol Brain Res. 1997; 47(1-2):59-66).

The neurophysiological role of $P2X_3$ receptors in sensory nerve function in the airways is similar to that mediating somatic nociception (Undem B J and Nassenstein C: Airway nerves and dyspnea associated with inflammatory airway disease, Respir Physiol Nerobiol 167: 36-44, 2009). This similarity has driven hypotheses concerning the involvement of $P2X_3$ receptors in the symptoms of airway dysfunction including cough and bronchial hyper-reactivity (Ford A P: In pursuit of $P2X_3$ antagonists: novel therapeutics for chronic pain and afferent sensitization, Purinergic signal 8 (suppl 1):3-26, 2012; North R A, Jarvis M F P2X Receptors as Drug Targets; Mol Pharmacol, 83:759-769, 2013). $P2X_3$ subunits are also co-localized in many neurons, particularly within DRG, nodose ganglia, nucleus tractus solitarius, and taste buds (Cheung K K, Burnstock G: Localization of $P2X_3$ receptors and coexpression with P2X2 receptors during rat embryonic neurogenesis. J Comp Neurol 443(4):368-382 2002)

$P2X_3$ antagonists have been proposed for the treatment of diabetic neuropathic pain (Guo J et al: Contributions of purinergic $P2X_3$ receptors within the midbrain periaqueductal gray to diabetes-induced neuropathic pain, J Physiol Sci January; 65(1):99-104 2015).

$P2X_3$ and $P2X_{2/3}$ channels play an important role in the development of articular hyperalgesia of arthritic joints (Teixeira J M et al: $P2X_3$ and $P2X_{2/3}$ Receptors Play a Crucial Role in Articular Hyperalgesia Development Through Inflammatory Mechanisms in the Knee Joint Experimental Synovitis, Mol Neurobiol October; 54(8): 6174-6186, 2017).

$P2X_3$ are also a potential target for therapeutic treatment of bladder pain. They were also proposed to be analgesic targets to treat ureteral colicky pain and to facilitate ureteral stone passage (Canda A E et al: Physiology and pharmacology of the human ureter: basis for current and future treatments, Urol Int. 78(4):289-98, 2007).

$P2X_3$ over-expression is involved in poor recurrence-free survival in hepatocellular carcinoma patients and identifies the $P2X_3$ as a potential therapeutic target (Maynard J P et al: $P2X_3$ purinergic receptor overexpression is associated with poor recurrence-free survival in hepatocellular carcinoma patients Oncotarget December 1; 6(38):41162-79, 2015).

It has been suggested that $P2X_3$ antagonists may improve recovery of erectile function (Li C L et al: Effects of intracavernous injection of $P2X_3$ and NK1 receptor antagonists on erectile dysfunction induced by spinal cord transection in rats, Andrologia. February; 47(1):25-9, 2015).

ATP enhances citric acid-evoked and histamine-evoked cough in preclinical models, effects that can be attenuated by $P2X_3$ selective antagonists (Kamei J and Takahashi Y: Involvement of ionotropic purinergic receptors in the histamine-induced enhancement of the cough reflex sensitivity in guinea pigs, October 10; 547(1-3):160-4, 2006). In humans, local delivery of ATP initiates cough and bronchospasm (Basoglu O K et al: Effects of aerosolized adenosine 5'-triphosphate vs adenosine 5'-monophosphate on dyspnea and airway caliber in healthy nonsmokers and patients with asthma, Chest. October; 128(4):1905-9, 2005).

The therapeutic promise of $P2X_3$ antagonists for the treatment of chronic cough was first recognized by Ford and Undem (Ford A P, Undem B J: The therapeutic promise of ATP antagonism at $P2X_3$ receptors in respiratory and urological disorders, Front Cell Neurosci, December 19; 7:267, 2013). $P2X_3$ are expressed by airway afferent nerves and mediate hypersensitivity of the cough reflex, which is dramatically reduced by the oral $P2X_3$ antagonist, AF-219 (Abdulgawi et al: $P2X_3$ receptor antagonist (AF-219) in refractory chronic cough: a randomised, double-blind, placebo-controlled phase 2 study, Lancet 385, 1198-205, 2015).

ATP is a key neurotransmitter in the taste system, acting largely via $P2X_{2/3}$ heteromultimer receptors. Consequently, disruption of taste function may be an unintentional consequence of therapeutic trials of pain, chronic cough and other conditions using purinergic $P2X_3$ antagonists (Vandenbeuch A et al: Role of the ectonucleotidase NTPDase2 in taste bud function, Proc Natl Acad Sci USA, September 3; 110(36): 14789-94, 2013. Bo X et al: Localization of ATP-gated P2X2 and $P2X_3$ receptor immunoreactive nerves in rat taste buds, Neuroreport, 10(5):1107-11, 1999).

Various compounds have been described in the literature as $P2X_3$ and/or $P2X_{2/3}$ Inhibitors.

WO2017058645 (Afferent Pharmaceuticals INC) discloses the use of diaminopyrimidine $P2X_3$/$P2X_{2/3}$ antagonists for the treatment of disorders including cough, chronic cough and urge to cough, including cough associated with a respiratory disease or disorder, administering an efficacious amount of the compound disclosed. However, phthalazine derivatives are not disclosed.

WO2017011729 (Patara Pharma LLC), discloses the use of cromolyn or a pharmaceutically acceptable salt thereof and $P2X_3$ and/or a $P2X_{2/3}$ receptor antagonist as antitussive agent, for the treatment of lung diseases and conditions.

WO2016091776, (Evotec AG), discloses 1,3-thiazol-2-yl substituted benzamide compounds that inhibit $P2X_3$ receptor and to pharmaceutical compositions containing such compounds, and the use of compounds for the treatment of several disorders, including the respiratory diseases.

WO2016088838 (Shionogi), discloses purine derivatives compounds having a novel $P2X_3$ and/or $P2X_{2/3}$ receptor antagonizing effect.

WO2016084922, (Shionogi), discloses triazine derivatives compounds having a novel $P2X_3$ and/or $P2X_{2/3}$ receptor antagonizing effect WO2008123963 (Renovis) relates to fused heterocyclic compounds of the class tetrahydropyrido[4,3-d]pyrimidines and pharmaceutical compositions comprising such compounds. Also provided are methods for preventing and/or treating several disorders, such as neurodegenerative disorders, pain, asthma, autoimmune disorders administering the disclosed compounds.

WO2008130481 (Renovis) discloses 2-cyanophenyl fused heterocyclic compounds of the class tetrahydropyrido [4,3-d]pyrimidines and pharmaceutical compositions comprising such compounds.

WO2010033168 (Renovis) discloses a series of benzamides substituted with phenyl or pyridyl which are stated to be useful for treatment of diseases associated with P2X purinergic receptors, and more particularly to $P2X_3$ receptor and/or $P2X_{2/3}$ receptor antagonists. However, phthalazine derivatives are not disclosed.

WO2009110985 (Renovis) relates to phenyl- and pyridyl-substituted benzamide compounds and pharmaceutical compositions comprising such compounds, but not thiazole-substituted benzamides, rendering said compounds different from the compounds of the present invention.

WO2008000645 (Roche) discloses tetrazole substituted arylamides compounds antagonists of $P2X_3$ and/or $P2X_{2/3}$ receptors, useful for the treatment of genitourinary, pain, gastrointestinal and respiratory diseases, conditions and disorders.

Despite the above cited prior art, there is still the need of novel phthalazine derivatives compounds for treatment of diseases associated with $P2X_3$ receptors in many therapeutic areas such as in particular the respiratory diseases, preferably having a selective action on the $P2X_3$ receptor to avoid the side effect on taste.

Of note, the state of the art does not describe or suggest phthalazine derivatives compounds of general formula (I) of the present invention which represent a solution to the aforementioned need.

SUMMARY OF THE INVENTION

The present invention refers to compounds of formula (I)

(I)

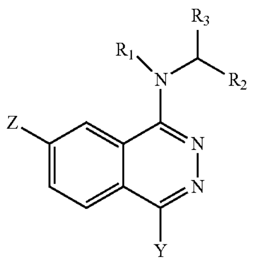

wherein

Z is selected from the group consisting of (5-6 membered)-heteroaryl and aryl, wherein any of such heteroaryl and aryl may be optionally substituted by one or more groups selected from $(C_1-C_3)$alkyl- and halo;

$R_1$ is H or $(C_1-C_4)$alkyl;

$R_2$ is selected from the group consisting of heteroaryl and $(C_3-C_8)$cycloalkyl-, wherein any of such heteroaryl may be optionally substituted by one or more groups selected from $(C_1-C_3)$alkyl, $(C_1-C_6)$haloalkyl and halo;

$R_3$ is H or $(C_1-C_4)$alkyl;

Y is selected from the group consisting of H, $(C_1-C_4)$alkyl-, $(C_3-C_8)$cycloalkyl-, $(C_3-C_8)$heterocycloalkyl, $(C_3-C_8)$heterocycloalkyl-$(C_1-C_4)$alkyl-.

In a second aspect, the invention refers to a pharmaceutical composition comprising a compound of formula (I) or pharmaceutically acceptable salt thereof, either alone or in combination with another one or more active ingredient, in admixture with one or more pharmaceutically acceptable carrier or excipient.

In a third aspect, the invention provides a compound of formula (I) for the use as a medicament.

In a further aspect, the invention provides the use of a compound of formula (I) for use in treatment of any disease wherein the $P2X_3$ receptors are involved.

In a further aspect, the invention refers to a compound of formula (I) for use in the prevention and/or treatment of respiratory diseases including cough, sub-acute or chronic cough, treatment-resistant cough, idiopathic chronic cough, post-viral cough, iatrogenic cough, asthma, idiopathic pulmonary fibrosis (IPF), chronic obstructive pulmonary disease (COPD) and cough associated with respiratory diseases such as COPD, asthma and bronchospasm.

DETAILED DESCRIPTION OF THE INVENTION

Unless otherwise provided, the term compound of formula (I) comprises in its meaning stereoisomer, tautomer or pharmaceutically acceptable salt or solvate.

The term "pharmaceutically acceptable salts", as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

The term "halogen" or "halogen atoms" as used herein includes fluorine, chlorine, bromine, and iodine atom, preferably chlorine or fluorine.

The term "($C_x$-$C_y$) alkyl" wherein x and y are integers, refers to a straight or branched chain alkyl radical having from x to y carbon atoms. Thus, when x is 1 and y is 6, for example, the term includes methyl, ethyl, n-propyl, isopropyl, n-butyl, isobutyl, sec-butyl, t-butyl, n-pentyl and n-hexyl.

As used herein, the term "($C_x$-$C_y$)alkylene" wherein x and y are integers, refers to a $C_x$-$C_y$alkyl radical having in total two unsatisfied valencies, such as a divalent methylene radical.

The expressions "($C_x$-$C_y$) haloalkyl" wherein x and y are integers, refer to the above defined "$C_x$-$C_y$alkyl" groups wherein one or more hydrogen atoms are replaced by one or more halogen atoms, which can be the same or different.

Examples of said "($C_x$-$C_y$) haloalkyl" groups may thus include halogenated, poly-halogenated and fully halogenated alkyl groups wherein all of the hydrogen atoms are replaced by halogen atoms, e.g. trifluoromethyl or difluoro methyl, trifluoroethyl groups.

By way of analogy, the terms "($C_1$-$C_6$) hydroxyalkyl" or "($C_1$-$C_6$) aminoalkyl" refer to the above defined "($C_1$-$C_6$) alkyl" groups wherein one or more hydrogen atoms are replaced by one or more hydroxy (OH) or amino group respectively. Examples include respectively hydroxymethyl, aminomethyl, dimethylaminopropyl and the like.

In the present description, unless otherwise provided, the aminoalkyl encompasses alkyl groups (i.e. "($C_1$-$C_6$) alkyl" groups) substituted by one or more amino group (—$NR^AR^B$). Thus, an example of aminoalkyl is a mono-aminoalkyl group such as $R^AR^BN$—($C_1$-$C_6$) alkyl.

The term "($C_x$-$C_y$) cycloalkyl" wherein x and y are integers, refers to saturated cyclic hydrocarbon groups containing the indicated number of ring carbon atoms. Examples include cyclopropyl, cyclobutyl, cyclopentyl, cyclohexyl, cycloheptyl.

The term "aryl" refers to mono cyclic carbon ring systems which have 6 ring atoms wherein the ring is aromatic. Examples of suitable aryl monocyclic ring systems include, for instance, phenyl.

The term "heteroaryl" refers to a mono- or bi-cyclic aromatic radical containing one or more heteroatoms selected from S, N and O, and includes radicals having two such monocyclic rings, or one such monocyclic ring and one monocyclic aryl ring, which are fused through a common bond. Examples of suitable 5,6-membered heteroaryl are: are thienyl, furyl, pyrrolyl, imidazolyl, thiazolyl, isothiazolyl, pyrazolyl, oxazolyl, isoxazolyl, isothiazolyl, triazolyl, thiadiazolyl, oxadiazolyl, pyridinyl, pyridazinyl, pyrimidinyl, pyrazinyl, tetrazolyl and triazinyl.

The term "heterocyclyl" or "heterocyclic" relate to a saturated mono-, bi- or tri-cyclic non-aromatic radical containing one or more heteroatoms selected from S, N and O. In the case of bicyclic heterocyclic systems, included within the scope of the term are fused, spiro and bridged bicyclic systems.

The term "($C_x$-$C_y$) heterocycloalkyl" wherein x and y are integers, refers to saturated or partially unsaturated monocyclic ($C_x$-$C_y$) cycloalkyl groups in which at least one ring carbon atom is replaced by at least one heteroatom (e.g. N, S or O) or may bear an -oxo (=O) substituent group. Said heterocycloalkyl (i.e. heterocyclic radical or group) may be further optionally substituted on the available positions in the ring, namely on a carbon atom, or on an heteroatom available for substitution. Substitution on a carbon atom includes spiro disubstitution as well as substitution on two adjacent carbon atoms, in both cases thus form additional condensed 5 to 6 membered heterocyclic ring. Examples of ($C_x$-$C_y$) heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydrothiophenyl, azetidinyl, oxetanyl, tetrahydropyranyl, pyranyl, 2H- or 4H-pyranyl, dihydro- or tetrahydrofuranyl, dihydroisoxazolyl, pyrrolidin-2-one-yl, dihydropyrrolyl radicals and the like.

Specific examples of said heterocycle radicals are tetrahydrothiophene 1,1-dioxide, 3,3-difluoropyrrolidinyl, 1-pyrrolidinyl, 1-methyl-2-pyrrolidinyl, 1-piperidinyl, 1-piperazinyl, 4-morpholinyl.

The expressions "Aryloxyl" and "Aryl ($C_1$-$C_6$) alkoxyl" likewise "heteroAryloxyl" and "Heteroaryl ($C_1$-$C_6$) alkoxyl" refer to Aryl or Heteroaryl groups attached through an oxygen bridge and chained Aryl-alkoxyl or HeteroAryl-alkoxyl groups. Examples of such groups are phenyloxy, benzyloxy and pyridinyloxy respectively.

The term "aryl ($C_1$-$C_6$) alkyl" refers to an aryl ring linked to a straight-chained or branched alkyl groups wherein the number of carbon atoms is from 1 to 6, e.g. phenylmethyl (i.e. benzyl), phenylethyl or phenylpropyl.

The term ($C_z$-$C_k$)heterocycloalkyl-($C_x$-$C_y$)alkyl wherein z and k are integers, refers to an heterocyclic ring linked to a straight-chained or branched alkyl groups having from x to y carbon atoms.

Likewise, the term "heteroaryl ($C_x$-$C_y$)alkyl" or "aryl ($C_x$-$C_y$)alkyl" refers to an heteroaryl or aryl ring linked to a straight-chained or branched alkyl groups having from x to y carbon atoms.

The expression "ring system" refers to mono- or bicyclic or polycyclic ring systems which may be saturated, partially unsaturated or unsaturated, such as aryl, ($C_3$-$C_{10}$) cycloalkyl, ($C_3$-$C_6$)heterocycloalkyl or heteroaryl.

The terms "group", "radical" or "fragment" or "substituent" are synonymous and are intended to indicate functional groups or fragments of molecules attachable to a bond or other fragments or molecules. Thus, as an example, a "heterocyclic radical" herein refers to a mono- or bi-cyclic saturated or partially saturated heterocyclic moiety (group, radical), preferably a 4 to 11 membered monocyclic radical, at least one further ring carbon atom in the said heterocyclic radical is optionally replaced by at least one further heteroatom independently selected from N, S or O and/or may bear an -oxo (=O) substituent group, said heterocyclic radical is further optionally including spiro disubstitution as well as substitution on two adjacent or vicinal atoms forming an additional 5 to 6 membered cyclic or heterocyclic, saturated, partially saturated or aromatic ring. Examples of said heterocycle radicals are 1-pyrrolidinyl, 1-piperidinyl, 1-piperazinyl, 4-morpholinyl and the like.

A dash ("-") that is not between two letters or symbols is meant to represent the point of attachment for a substituent. When graphically represented the point of attachment in a cyclic functional group is indicated with a dot ("•") localized in one of the available ring atom where the functional group is attachable to a bond or other fragment of molecules.

An oxo moiety is represented by (O) as an alternative to the other common representation, e.g. (=O). Thus, in terms of general formula, the carbonyl group is herein represented as —C(O)—, in general, the bracketed group is a lateral group, not included into the chain, and brackets are used, when deemed useful, to help disambiguating linear chemical formulas; e.g. the sulfonyl group —$SO_2$— might be also represented as —$S(O)_2$— to disambiguate e.g. with respect to the sulfinic group —S(O)O—.

Whenever basic amino or quaternary ammonium groups are present in the compounds of formula I, physiologically acceptable anions may be present, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate. Likewise, in the presence of acidic groups such as COOH groups, corresponding physiological cation salts may be present as well, for instance including alkaline or alkaline earth metal ions.

It will be apparent that compounds of formula (I) when contain one or more stereogenic center, may exist as optical stereoisomers.

Where the compounds according to the invention have at least one stereogenic center, they may accordingly exist as enantiomers. Where the compounds according to the invention possess two or more stereogenic centers, they may additionally exist as diastereoisomers. All such single enantiomers, diastereoisomers and mixtures thereof in any proportion are encompassed within the scope of the present invention. The absolute configuration (R) or (S) for carbon bearing a stereogenic center is assigned on the basis of Cahn-Ingold-Prelog nomenclature rules based on groups' priorities.

The invention further concerns the corresponding deuterated derivatives of compounds of formula (I).

All preferred groups or embodiments described above and herebelow for compounds of formula I may be combined among each other and apply as well mutatis mutandis.

As above indicated, the present invention refers to a series of compounds represented by the general formula (I) as herein below described in details, which are endowed with an antagonist property versus receptor $P2X_3$.

Differently from similar compounds of the prior art, the compounds of formula (I) of the present invention are able to act as antagonist $P2X_3$ in a substantive and effective way, particularly appreciated by the skilled person when looking at a suitable and efficacious compounds useful for the treatment of respiratory disease, in particular chronic cough.

As indicated in the experimental part, the compounds of formula (I) have an activity as shown in Table 2, wherein for each compound is reported the potency expressed as half maximal inhibitory concentration ($pIC_{50}$) on receptors.

As further advantage, the compound of formula (I) have surprisingly been found to effectively and selectively inhibit mainly the $P2X_3$ receptor and said compounds are useful for the treatment of respiratory disease avoiding adverse effect, such as loss of taste response. In fact, as it can be appreciated in Table 3, the compounds of formula (I) show a greater activity versus the receptor $P2X_3$ in comparison to the receptor $P2X_{2/3}$.

Thus, in one aspect the present invention relates to a compound of general formula (I) as $P2X_3$ antagonist (I)

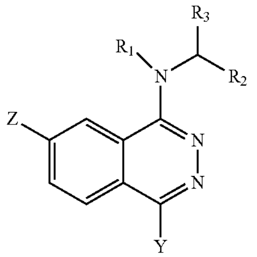

wherein

Z is selected from the group consisting of (5-6 membered)-heteroaryl and aryl, wherein any of such heteroaryl and aryl may be optionally substituted by one or more groups selected from $(C_1-C_3)$alkyl- and halo;

$R_1$ is H or $(C_1-C_4)$alkyl;

$R_2$ is selected from the group consisting of heteroaryl and $(C_3-C_8)$cycloalkyl-, wherein any of such heteroaryl may be optionally substituted by one or more groups selected from $(C_1-C_3)$alkyl, $(C_1-C_6)$haloalkyl and halo;

$R_3$ is H or $(C_1-C_4)$alkyl;

Y is selected from the group consisting of H, $(C_1-C_4)$ alkyl-, $(C_3-C_8)$cycloalkyl-, $(C_3-C_8)$heterocycloalkyl, $(C_3-C_8)$heterocycloalkyl-$(C_1-C_4)$alkyl-.

In a preferred embodiment Z is aryl or (5-6 membered)-heteroaryl wherein the heteroaryl is selected from the group consisting of thiazole, pyridine, pyrimidine and pyrazole.

In a preferred embodiment $R_2$ is heteroaryl or $(C_3-C_8)$ cycloalkyl- wherein the heteroaryl is selected from the group consisting of pyridazine, pyrimidine and oxadiazole, and the $(C_3-C_8)$cycloalkyl- is cyclopropyl.

In a preferred embodiment, the invention refers to at least one of the compounds listed in the Table 1 below and pharmaceutical acceptable salts thereof.

TABLE 1

List of preferred compounds of Formula (I)

| Ex. N. | Structure | Chemical Name |
|---|---|---|
| Example 1 | 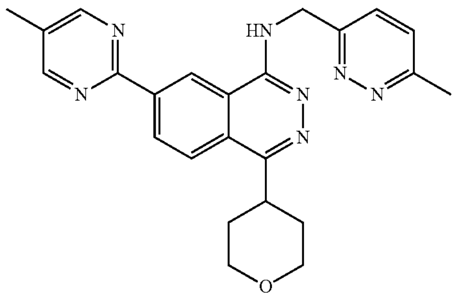 | N-((6-Methylpyridazin-3-yl)methyl)-7-(5-methylpyrimidin-2-yl)-4-(tetrahydro-2H-pyran-4-yl)phthalazin-1-amine |

TABLE 1-continued

| List of preferred compounds of Formula (I) | | |
|---|---|---|
| Ex. N. | Structure | Chemical Name |
| Example 2 | 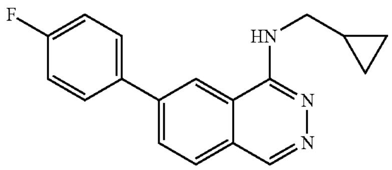 [SMILES: Fc1ccc(-c2ccc3cnnc(NCC4CC4)c3c2)cc1] | N-(Cyclopropylmethyl)-7-(4-fluorophenyl)phthalazin-1-amine |
| Example 3 | 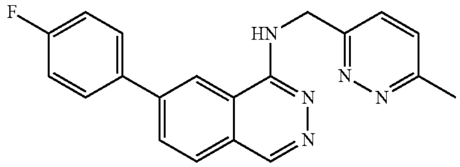 [SMILES: Cc1ccc(CNc2nncc3ccc(-c4ccc(F)cc4)cc23)nn1] | 7-(4-Fluorophenyl)-N-((6-methylpyridazin-3-yl)methyl)phthalazin-1-amine |
| Example 4 | 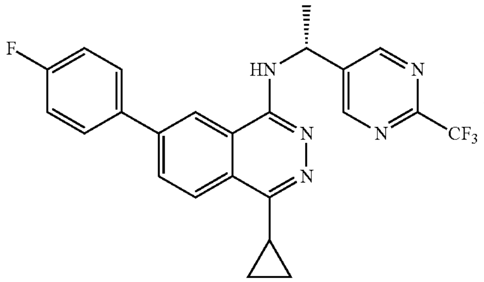 [SMILES: C[C@@H](Nc1nnc(C2CC2)c2ccc(-c3ccc(F)cc3)cc12)c1cnc(C(F)(F)F)nc1] | (R)-4-Cyclopropyl-7-(4-fluorophenyl)-N-(1-(2-(trifluoromethyl)pyrimidin-5-yl)ethyl)phthalazin-1-amine |
| Example 5 | 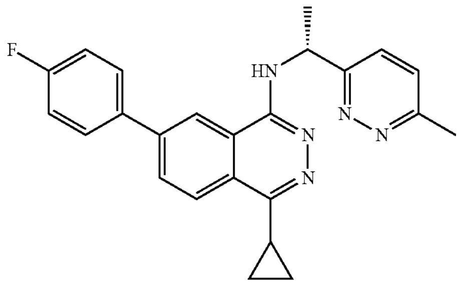 [SMILES: Cc1ccc([C@@H](C)Nc2nnc(C3CC3)c3ccc(-c4ccc(F)cc4)cc23)nn1] | (R)-4-Cyclopropyl-7-(4-fluorophenyl)-N-(1-(6-methylpyridazin-3-yl)ethyl)phthalazin-1-amine |
| Example 6 | 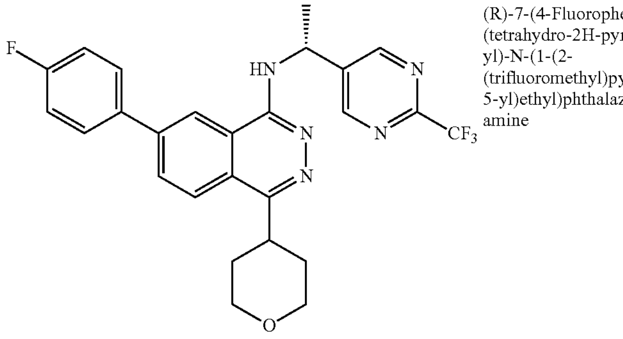 | (R)-7-(4-Fluorophenyl)-4-(tetrahydro-2H-pyran-4-yl)-N-(1-(2-(trifluoromethyl)pyrimidin-5-yl)ethyl)phthalazin-1-amine |

TABLE 1-continued

| List of preferred compounds of Formula (I) | | |
|---|---|---|
| Ex. N. | Structure | Chemical Name |
| Example 7 | 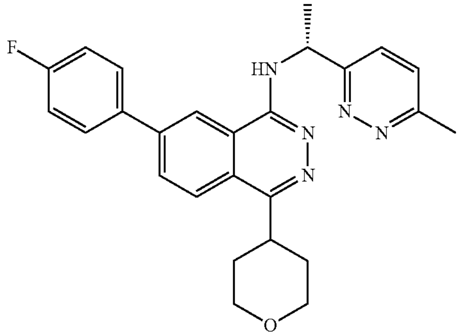 [SMILES: Cc1ccc([C@@H](C)Nc2nnc(C3CCOCC3)c3ccc(-c4ccc(F)cc4)cc23)nn1] | (R)-7-(4-Fluorophenyl)-N-(1-(6-methylpyridazin-3-yl)ethyl)-4-(tetrahydro-2H-pyran-4-yl)phthalazin-1-amine |
| Example 9 | 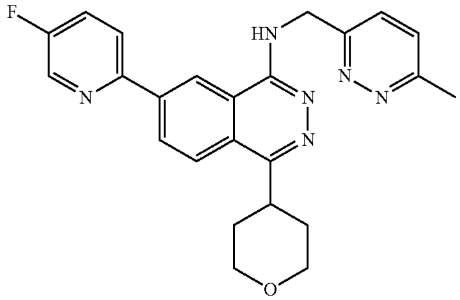 [SMILES: Cc1ccc(CNc2nnc(C3CCOCC3)c3ccc(-c4ccc(F)cn4)cc23)nn1] | 7-(5-Fluoropyridin-2-yl)-N-((6-methylpyridazin-3-yl)methyl)-4-(tetrahydro-2H-pyran-4-yl)phthalazin-1-amine |
| Example 10 | 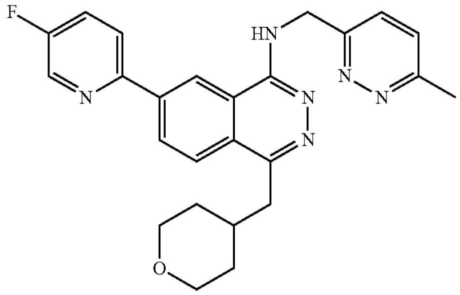 [SMILES: Cc1ccc(CNc2nnc(CC3CCOCC3)c3ccc(-c4ccc(F)cn4)cc23)nn1] | 7-(5-Fluoropyridin-2-yl)-N-((6-methylpyridazin-3-yl)methyl)-4-((tetrahydro-2H-pyran-4-yl)methyl)phthalazin-1-amine |
| Example 11 | 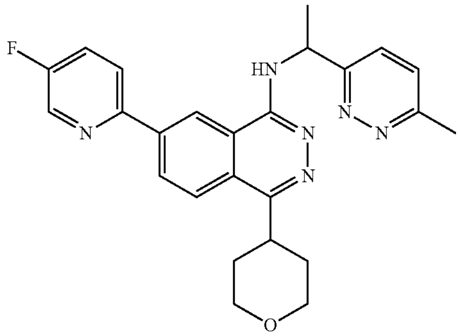 [SMILES: Cc1ccc(C(C)Nc2nnc(C3CCOCC3)c3ccc(-c4ccc(F)cn4)cc23)nn1] | Single enantiomer 1 of 7-(5-Fluoropyridin-2-yl)-N-(1-(6-methylpyridazin-3-yl)ethyl)-4-(tetrahydro-2H-pyran-4-yl)phthalazin-1-amine |
| Example 13 | 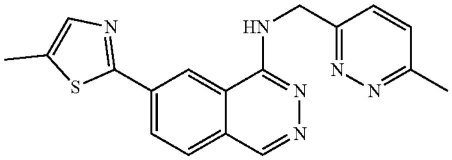 | N-[(6-Methylpyridazin-3-yl)methyl]-7-(5-methylthiazol-2-yl)phthalazin-1-amine |

TABLE 1-continued

| List of preferred compounds of Formula (I) | | |
|---|---|---|
| Ex. N. | Structure | Chemical Name |
| Example 14 | 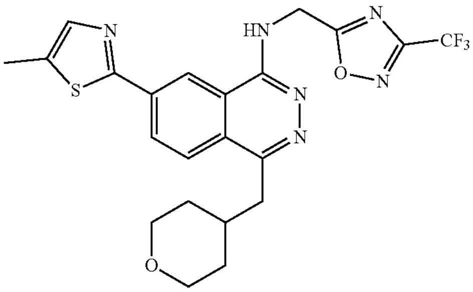 [SMILES: Cc1cnc(-c2ccc3c(CC4CCOCC4)nnc(NCc4nc(C(F)(F)F)no4)c3c2)s1] | 7-(5-Methylthiazol-2-yl)-4-((tetrahydro-2H-pyran-4-yl)methyl)-N-((3-(trifluoromethyl)-1,2,4-oxadiazol-5-yl)methyl)phthalazin-1-amine |
| Example 15 | 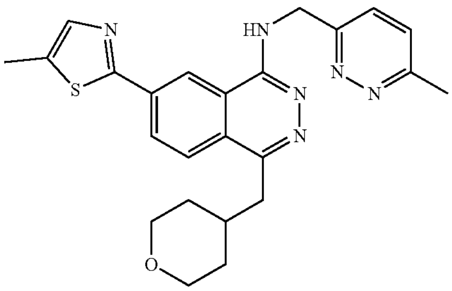 | N-((6-Methylpyridazin-3-yl)methyl)-7-(5-methylthiazol-2-yl)-4-((tetrahydro-2H-pyran-4-yl)methyl)phthalazin-1-amine |
| Example 16 | 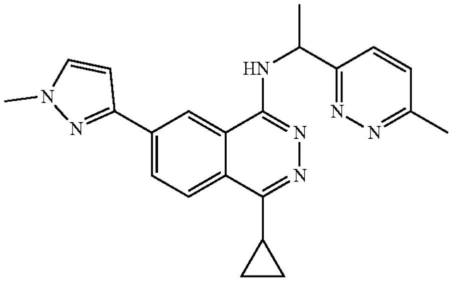 | Racemic mixture of 4-Cyclopropyl-7-(1-methyl-1H-pyrazol-3-yl)-N-(1-(6-methylpyridazin-3-yl)ethyl)phthalazin-1-amine |
| Example 17 | 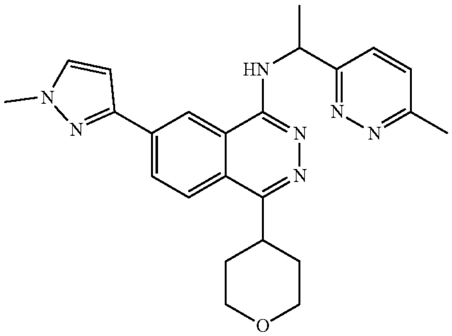 | 7-(1-Methylpyrazol-3-yl)-N-[1-(6-methylpyridazin-3-yl)ethyl]-4-tetrahydropyran-4-yl-phthalazin-1-amine |
| Example 19 | 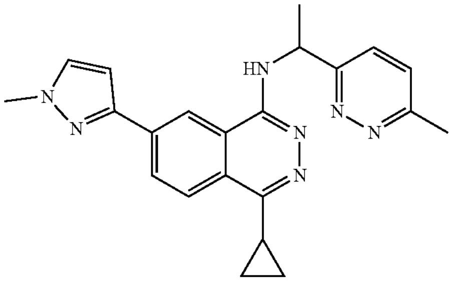 | Single enatiomer 2 of 4-Cyclopropyl-7-(1-methyl-1H-pyrazol-3-yl)-N-(1-(6-methylpyridazin-3-yl)ethyl)phthalazin-1-amine |

In one preferred embodiment, the invention refers to a compound of formula (I), wherein Y and $R_1$ are H, represented by the formula Ia (Ia)

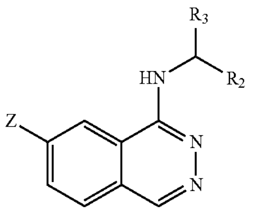

wherein

Z is selected from the group consisting of (5-6 membered)-heteroaryl and aryl, wherein any of such heteroaryl and aryl may be optionally substituted by one or more groups selected from $(C_1-C_3)$alkyl- and halo;

$R_2$ is selected from the group consisting of heteroaryl and $(C_3-C_8)$cycloalkyl-, wherein any of such heteroaryl may be optionally substituted by one or more $(C_1-C_3)$ alkyl-;

$R_3$ is H or $(C_1-C_4)$alkyl.

The compounds of formula (I) including all the compounds or at least one of the here above listed can be generally prepared according to the procedure outlined in detail in the Schemes shown below using generally known methods.

Scheme 1

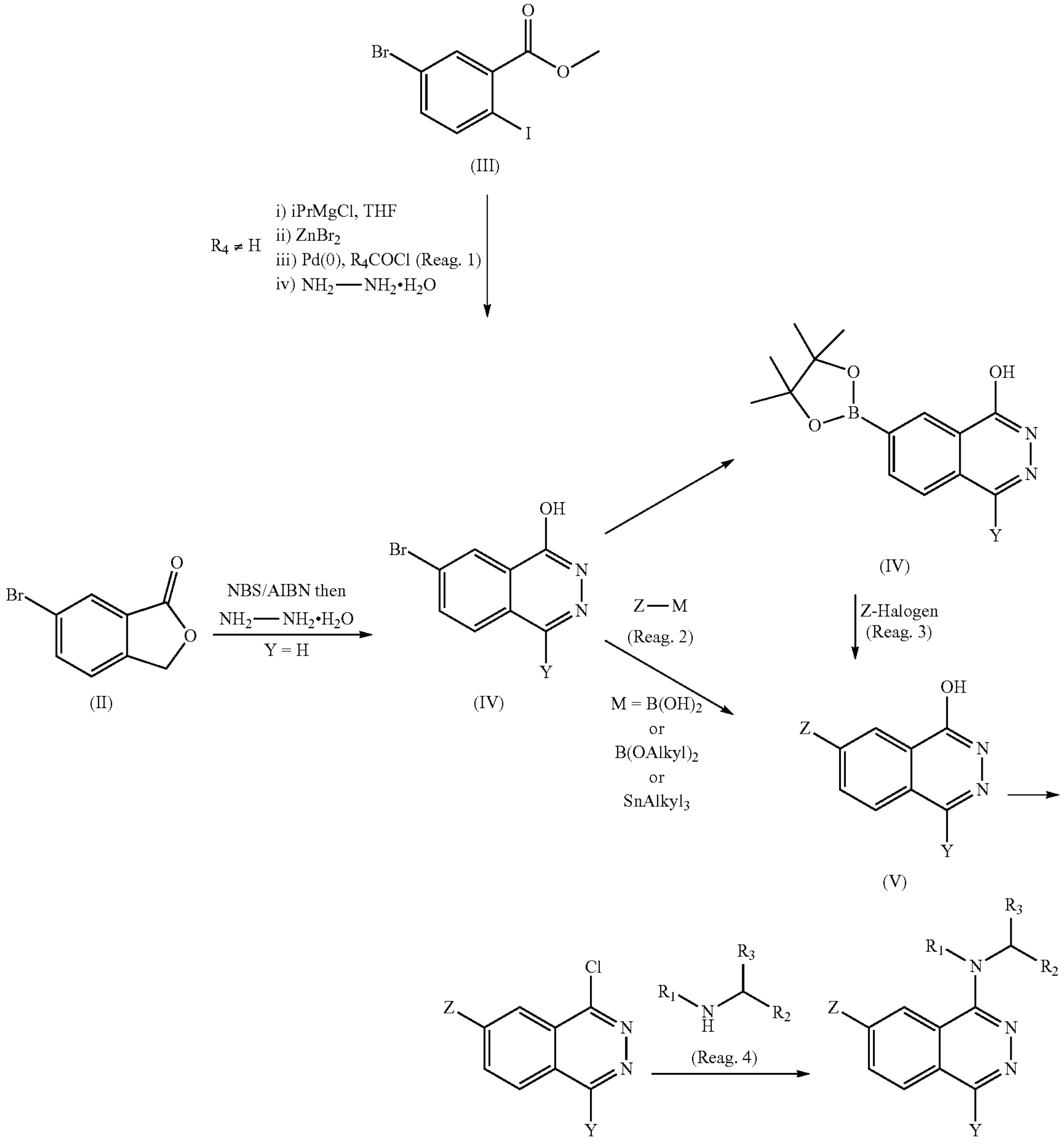

(VIII) (I)

In one embodiment of the present invention, compound of formula (I) may be prepared according to SCHEME 1 from compound (II).

Compound (IV) may be prepared from Compound (II) by a two-step ring closure reaction mediated by the NBS/hydrazine system.

Alternatively, Compound (IV) may be prepared from Compound (III) by a four-step sequence ring closing reaction as briefly described in Scheme 1.

Compound (VI) may be prepared from Compound (IV) by metal-catalyzed Miyaura borylation reaction.

Compound (V) may be prepared from Compound (IV) by a metal-catalyzed cross coupling reactions like Stille or Suzuki or similars as described in "Transition Metals for Organic Synthesis", 2nd Ed, 1, 2004 with a suitable reagent like (Reag. 3).

Alternatively, Compound (V) may be prepared from Compound (VI) by a metal-catalyzed cross coupling reactions like Stille or Suzuki or similars as described in "Transition Metals for Organic Synthesis", 2nd Ed, 1, 2004 with a suitable reagent like (Reag. 2).

Compound (VII) may be prepared from Compound (VI) by a deoxyahalogenation reaction mediated by reagents like, for example, Phosphorous oxychloride.

Compound of formula (I) may be prepared from Compound (VII) by a reaction with a suitable amine (Reag. 1) in the presence of a base like, for example TEA or DIPEA.

Some compounds of formula (I) may contain a protected hydroxyl or amino group which were then removed under well known procedures.

The compounds of the present invention have surprisingly been found to effectively inhibit $P2X_3$ receptor and said compounds are useful for the treatment of respiratory disease.

In one embodiment, representative compounds of formula (I) of the present invention have surprisingly been found to effectively and selectively inhibit $P2X_3$ receptor and said compounds are useful for the treatment of respiratory disease avoiding adverse effect, such as loss of taste response.

In a preferred embodiment, the compound of formula (I) are selective $P2X_3$ antagonist wherein the selective $P2X_3$ antagonist is at least 10-fold selective for $P2X_3$ homomeric receptor antagonism versus $P2X_{2/3}$ heteromeric receptor antagonism.

In a further preferred embodiment, the selective $P2X_3$ antagonist is at least 30-fold selective for $P2X_3$ homomeric receptor antagonism versus $P2X_{2/3}$ heteromeric receptor antagonism.

In a further preferred embodiment, the selective $P2X_3$ antagonist is at least 50-fold selective for $P2X_3$ homomeric receptor antagonism versus $P2X_{2/3}$ heteromeric receptor antagonism.

The present invention also provides a pharmaceutical composition comprising a compound of formula (I) or a pharmaceutically acceptable salt thereof in admixture with one or more pharmaceutically acceptable carrier or excipient, either alone or in combination with one or more further active ingredient.

In one aspect, the invention refers to a compound of formula (I) according to the invention for use as a medicament.

In a further aspect, the invention refers to the use of a compound of formula (I) of the invention, or a pharmaceutically acceptable salt thereof, in the manufacture of a medicament for the treatment of disorders associated with $P2X_3$ receptors mechanism, preferably for the treatment of respiratory diseases.

Preferably, the invention refers to a compound of formula (I) for use in the prevention and/or treatment of respiratory diseases, preferably cough, sub-acute or chronic cough, treatment-resistant cough, idiopathic chronic cough, post-viral cough, iatrogenic cough, asthma, idiopathic pulmonary fibrosis (IPF), chronic obstructive pulmonary disease (COPD) and cough associated with respiratory diseases such as COPD, asthma and bronchospasm.

More preferably, the invention refers to a compounds of formula (I) for use in the prevention and/or treatment of chronic cough and cough associated with respiratory diseases such as COPD, asthma and bronchospasm.

The invention also provides a method for the prevention and/or treatment of disorders associated with $P2X_3$ receptors mechanisms, said method comprising administering to a patient in need of such treatment a therapeutically effective amount of a compound of the invention.

In particular the invention refers to a method for the prevention and/or treatment wherein the disorder is cough, sub-acute or chronic cough, treatment-resistant cough, idiopathic chronic cough, post-viral cough, iatrogenic cough, asthma, idiopathic pulmonary fibrosis (IPF), chronic obstructive pulmonary disease (COPD) and cough associated with respiratory diseases such as COPD, asthma and bronchospasm, wherein said method comprises the administration of a proper amount of a compound of formula (I) to a patient in the need thereof.

In a further preferred embodiment, the disorder is chronic cough.

The methods of treatment of the invention comprise administering a safe and effective amount of a compound of formula (I) or a pharmaceutically acceptable salt thereof to a patient in need thereof. As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and it can nevertheless be routinely determined by the skilled artisan. The compounds of formula (I) or pharmaceutically acceptable salts thereof may be administered once or according to a dosing regimen wherein a number of doses are administered at varying intervals of time for a given period of time. Typical daily dosages may vary depending upon the particular route of administration chosen.

The invention also provides pharmaceutical compositions of compounds of formula (I) in admixture with one or more pharmaceutically acceptable carrier or excipient, for example those described in Remington's Pharmaceutical Sciences Handbook, XVII Ed., Mack Pub., N.Y., U.S.A.

Administration of the compounds of the invention and their pharmaceutical compositions may be accomplished according to patient needs, for example, orally, nasally, parenterally (subcutaneously, intravenously, intramuscularly, intrasternally and by infusion) and by inhalation.

Preferably the compounds of the present invention may be administered orally or by inhalation. More preferably the compounds of the present invention are administered orally.

Various solid oral dosage forms can be used for administering compounds of the invention including such solid forms as tablets, gelcaps, capsules, caplets, granules, lozenges and bulk powders. The compounds of the invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the invention.

Preferably the compounds of the invention are administered in forms of tablets.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the invention may be injected, for example, intravenously, in the form of an isotonic sterile solution.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers.

Preferably, the compound of the present invention are administered orally.

The compounds of the invention can be administered as the sole active agent or in combination with other pharmaceutical active ingredients.

Preferably, the compound of the present invention can be combined with therapeutic agents or active ingredients useful for the treatment of disease which are related to or mediated by $P2X_3$ receptor.

The dosages of the compounds of the invention depend upon a variety of factors including among others the particular disease to be treated, the severity of the symptoms, the route of administration, and the like.

The invention is also directed to a device comprising a pharmaceutical composition comprising a compound of formula (I) according to the invention, in form of a single- or multi-dose dry powder inhaler or a metered dose inhaler.

The various aspects of the invention described in this application are illustrated buy the following examples which are not meant to limit the invention in any way. following examples illustrate the invention.

The example testing experiments described herein serve to illustrate the present invention and the invention is not limited to the examples given.

PREPARATIONS OF INTERMEDIATES AND EXAMPLES

Chemical names were generated using the Dotmatics software. In some cases generally accepted names of commercially available reagents were used in place of Dotmatics software generated names.

All reagents, for which the synthesis is not described in the experimental part, are either commercially available, or are known compounds or may be formed from known compounds by known methods by a person skilled in the art.

(R)-1-(2-(trifluoromethyl)pyrimidin-5-yl)ethanamine hydrochloride and (R)-1-(6-methylpyridazin-3-yl)ethan-1-amine hydrochloride were prepared accordingly to the procedure described in WO2016/091776.

Abbreviation—Meaning $Et_2O$: diethyl ether;
$Et_3N$: triethyl amine;
TEA: triethyl amine;
DCC: N,N'-Dicyclohexylcarbodiimide;
PyBOP: (benzotriazol-1-yloxy)tripyrrolidinophosphonium hexafluorophosphate;
DMF: dimethylformamide;
EtOAc: Ethyl acetate;
RT: room temperature;
THF: tetrahydrofuran;
DCM: dichloromethane;
MeOH: methyl alcohol;
EtOH: ethylic alcohol;
TFA: Trifluoroacetic acid;
LC-MS: Liquid Chromatography/Mass Spectrometry;
HPLC: high pressure liquid chromatography;
MPLC: medium pressure liquid chromatography;
SFC: Supercritical Fluid Chromatography;
dppf: 1,1'-Bis(diphenylphosphino) ferrocene;
$MgSO_4$: Magnesium sulfate
DIEA or DIPEA: N,N-Diisopropylethylamine;
MeCN: Acetonitrile;
MTBE: tert-Butyl methyl ether;
TBDMSCl: tert-Butyl(chloro)dimethylsilane;
DMSO: Dimethylsulfoxide;
$Boc_2O$: di-tert-butyl dicarbonate;
UPLC: Ultra Performance Liquid Chromatography.

General Experimental Details and Methods

Analytical Methods

Liquid Chromatography-Mass Spectrometry

Method 1

UPLC-MS was performed on a Waters DAD+Waters SQD2, single quadrapole UPLC-MS spectrometer using an Acquity UPLC BEH Shield RP18 1.7 um 100×2.1 mm (Plus guard cartridge), maintained at temp column being initially held at 5% acetonitrile/water (with 10 mM ammonium bicarbonate in each mobile phase) for 0.4 minutes, followed by a linear gradient of 5-95% within 6.4 minutes and then held at 95% for 1.2 minutes (F=0.4 mL/min).

Method 2

UPLC-MS was performed on a Waters DAD+Waters SQD2, single quadrapole UPLC-MS spectrometer using an Acquity UPLC BEH Shield RP18 1.7 um 100×2.1 mm (Plus guard cartridge), maintained at temp column being initially held at 5% Acetonitrile (Far UV grade) with 0.1% (V/V) formic acid/Water (High purity via PureLab Option unit) with 0.1% formic acid for 0.4 minutes, followed by a linear gradient of 5-95% within 6.4 minutes and then held at 95% for 1.2 minutes (F=0.4 mL/min).

NMR

[1]H Nuclear magnetic resonance (NMR) spectroscopy was carried out using a Bruker or Varian instruments operating at 400 MHz using the stated solvent at around RT unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Preparative Reverse-Phase HPLC Conditions

Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector. The columns used for the preparative purification of the compounds were a Waters Sunfire OBD Phenomenex Luna Phenyl Hexyl or Waters Xbridge Phenyl at 10 μm 19×150 mm or Waters CSH Phenyl Hexyl, 19×150, 5 μm column. Appropriate focused gradients were selected based on acetonitrile and MeOH solvent systems under either acidic or basic conditions. The modifiers used under acidic/basic conditions were formic acid or trifluoroacetic acid (0.1% V/V) and ammonium bicarbonate (10 mM) respectively. The purification was controlled by Waters Fractionlynx software through monitoring at 210-400 nm, and triggered a threshold collection value at 260 nm and, when using the Fractionlynx, the presence of target molecular ion as observed under API conditions. Collected fractions were analysed by LCMS (Waters Acquity systems with Waters SQD).

Chiral Supercritical Fluid Chromatography (SFC) Separation Protocol

The diastereomeric separation of compounds was achieved by Supercritical Fluid Chromatography (SFC) using a Waters Thar Prep100 preparative SFC system (P200 CO2 pump, 2545 modifier pump, 2998 UV/VIS detector, 2767 liquid handler with Stacked Injection Module). The Waters 2767 liquid handler acted as both auto-sampler and fraction collector. Appropriate isocratic methods were selected based on MeOH, EtOH or isopropanol solvent systems under un-modified or basic conditions. The standard SFC method used was modifier, CO2, 100 mL/min, 120 Bar backpressure, 40° C. column temperature. The modifier used under basic conditions was diethylamine (0.1% V/V). The modifier used under acidic conditions was either formic acid (0.1% V/V) or trifluoroacetic acid (0.1% V/V). The SFC purification was controlled by Waters Fractionlynx software through monitoring at 210-400 nm and triggered at a threshold collection value, typically 260 nm. Collected fractions were analysed by SFC (Waters/Thar SFC systems with Waters SQD). The fractions that contained the desired product were concentrated by vacuum centrifugation.

Supercritical Fluid Chromatography—Mass Spectrometry Analytical Conditions

Method 3

SFC-MS was performed on a Waters/Thar SFC systems with Waters SQD using a YMC Amylose-C column with a 20% methyl alcohol/$CO_2$ (with 0.1% diethylamine) isocratic run at 5 mL/min, 120 Bar backpressure, 40° C. column temperature.

Method 4

SFC-MS was performed on a Waters/Thar SFC systems with Waters SQD using a YMC Amylose-C column with a 30% methyl alcohol/$CO_2$ (with 0.1% diethylamine) isocratic run at 5 mL/min, 120 Bar backpressure, 40° C. column temperature.

Method 5

SFC-MS was performed on a Waters/Thar SFC systems with Waters SQD using a YMC Cellulose-C column with a 15% methyl alcohol/$CO_2$ (with 0.1% diethylamine) isocratic run at 5 mL/min, 120 Bar backpressure, 40° C. column temperature.

Method 6

SFC-MS was performed on a Waters/Thar SFC systems with Waters SQD using a Lux Cellulose-4 column with a 30% iso-propyl alcohol/$CO_2$ (with 0.1% diethylamine) isocratic run at 5 mL/min, 120 Bar backpressure, 40° C. column temperature.

Method 7

SFC-MS was performed on a Waters/Thar SFC systems with Waters SQD using a YMC Cellulose-C column with a 40% iso-propyl alcohol/$CO_2$ (with 0.1% diethylamine) isocratic run at 5 mL/min, 120 Bar backpressure, 40° C. column temperature.

Intermediate 1

7-Bromo-N-((6-methylpyridazin-3-yl)methyl)isoquinolin-1-amine

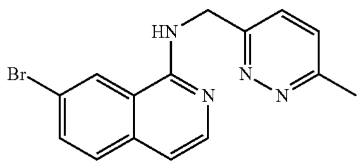 [SMILES: Cc1ccc(CNc2nccc3ccc(Br)cc23)nn1]

7-Bromo-1-chloroisoquinoline (100 mg, 0.412 mmol), potassium carbonate (171 mg, 1.24 mmol) and 6-methylpyridazin-3-yl)methanamine hydrochloride (121 mg, 0.619 mmol) were dissolved in NMP (1 mL). The reaction mixture was heated at 145° C. for 60 minutes in a microwave reactor. Saturated aqueous sodium chloride solution (10 mL) was added and the crude was extracted with a mixture of chloroform/2-propanol (60:40) (3×20 mL). The organic layer was dried over dried over MgSO4 and the solvent was removed in vacuo. The residue was purified by chromatography on silica eluting with −0-20% MeOH in DCM to give the title compound as an off-white solid (70 mg, 50%).

LCMS (Method 2): [MH+]=329.0 at 2.56 min.

Intermediate 2

7-Bromophthalazin-1-ol

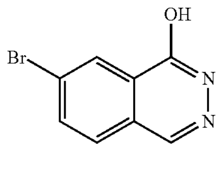 [SMILES: Oc1nncc2ccc(Br)cc12]

A mixture of 6-bromoisobenzofuran-1(3H)-one (1 g, 4.69 mmol), N-bromosuccinimide (919 mg, 5.16 mmol) and AIBN (81 mg, 0.491 mmol) in 1,2-dichloroethane (25 mL) was heated at reflux for two hours, cooled to RT and evaporated. The residue was washed with water (5 mL) and the resultant yellow gum heated in water (24 mL) at reflux for three hours then cooled to RT. The precipitated solid was filtered, washed with water and air dried. The solid was dissolved in 2-propanol (25 mL) and 65% hydrazine hydrate (1.9 mL) was added. The resulting mixture was heated at reflux for 2.5 h. The mixture was cooled, filtered, the solid was washed with water (5 mL) and dried to afford the title compound as a colourless solid (637 mg, 60%).

$^1$H NMR (400 MHz, DMSO): δ 12.90-12.80 (m, 1H), 8.44 (s, 1H), 8.38-8.35 (m, 1H), 8.20-8.15 (m, 1H), 7.99-7.94 (m, 1H).

Intermediate 3

7-(4-Fluorophenyl)phthalazin-1-ol

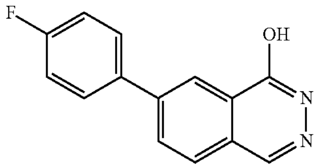 [SMILES: Oc1nncc2ccc(-c3ccc(F)cc3)cc12]

Nitrogen gas was bubbled for 5 minutes through a mixture of 7-bromophthalazin-1-ol (Intermediate 2) (250 mg, 1.11 mmol), 4-fluorobenzeneboronic acid (187 mg, 1.33 mmol), potassium carbonate (461 mg, 3.33 mmol) in 1,4-dioxane (5 mL)/water (1 mL) and Pd(dppf)Cl2 (41 mg, 0.056 mmol). The mixture was heated at 115° C. for 1.5 h. The mixture was cooled, diluted with EtOAc (30 mL). The organic phase was separated, concentrated in vacuo and the residue was purified by chromatography on silica eluting with 0-10% MeOH in DCM gradient to afford the title compound as a pale pink solid (241 mg, 90%).

$^1$H NMR (400 MHz, CDCl3): δ 10.22 (s, 1H), 8.61 (s, 1H), 8.21-8.19 (m, 1H), 8.06-8.02 (m, 1H), 7.82-7.79 (m, 1H), 7.73-7.66 (m, 2H), 7.24-7.16 (m, 2H).

Intermediate 4

7-bromo-4-cyclopropylphthalazin-1-ol

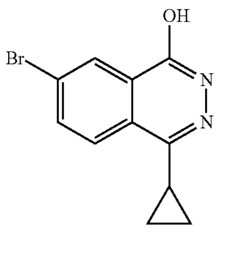 [SMILES: Oc1nnc(C2CC2)c2ccc(Br)cc12]

Isopropyl magnesium chloride (3.2 mL, 6.45 mmol, 2 M in THF) was added dropwise to a stirred solution of methyl 5-bromo-2-iodobenzoate (2.00 g, 5.87 mmol) in THE (40 mL) at −78° C. under nitrogen. The resulting mixture was stirred at 0° C. for 30 minutes under nitrogen atmosphere then anhydrous zinc bromide (1.45 g, 6.45 mmol) was added and the resulting precipitate was stirred for 15 minutes at 0° C. Cyclopropanecarbonyl chloride (0.64 ml, 7.04 mmol) and tetrakis(triphenylphosphine)palladium(0) (0.34 g, 0.29 mmol) were added and the mixture heated at 60° C. for 2 hours. The reaction mixture was cooled to RT and quenched by the addition of an aqueous saturated ammonium chloride solution (50 mL). The resultant solution was extracted with Et2O (2×75 mL). The organic layers were combined and washed with water, passed through a hydrophobic frit and the solvent was removed in vacuo to yield a yellow gum. To a solution of the residue in EtOH (40 mL) was added hydrazine hydrate (0.20 mL, 6.45 mmol) dropwise and the mixture was stirred at RT for 2 hours. The solvent was removed in vacuo, the residue was purified by chromatography on silica gel eluting with 5-100% EtOAc in isohexane to afford the title compound as a pale yellow solid (614 mg, 39%).

$^1$H NMR (400 MHz, CDCl3): δ 9.80 (br s, 1H), 8.59 (d, J=1.6 Hz, 1H), 8.02-7.95 (m, 2H), 2.24-2.15 (m, 1H), 1.04-0.99 (m, 4H). LCMS (Method 2): [MH+]=265 at 1.54 min.

The following intermediates reported in the table below were prepared according to the procedure described for the preparation of 7-bromo-4-cyclopropylphthalazin-1-ol.

| Intermediate No. | Chemical Name Structure | Analytical data $^1$H NMR LC-MS |
|---|---|---|
| Intermediate 5 | 7-Bromo-4-(tetrahydro-2H-pyran-4-yl)phthalazin-1-ol 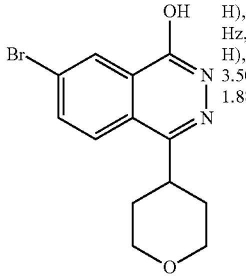 | $^1$H NMR (400 MHz, MeOD): δ 8.53 (s, 1 H),8.11 (d, J = 2.0 Hz, 1 H), 8.07 (dd, J = 2.1, 8.7 Hz, 1 H), 4.10-4.06 (m, 2 H), 3.74-3.67 (m, 2 H), 3.50-3.55 (m, 1 H), 2.09-1.88 (m, 4 H). |
| Intermediate 6 | 7-Bromo-4-((tetrahydro-2H-pyran-4-yl)methyl)phthalazin-1-ol 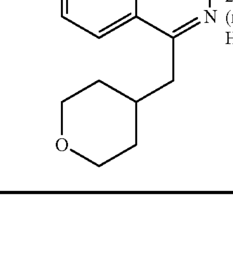 | $^1$H NMR (400 MHz, $CHCl_3$): δ 8.61 (d, J = 2.0 Hz, 1 H), 7.95 (dd, J = 2.1, 8.7 Hz, 1 H), 7.67 (d, J = 8.7 Hz, 1 H), 3.97 (dd, J = 4.0, 10.7 Hz, 2 H), 3.41-3.33 (m, 2 H), 2.84 (d, J = 7.0 Hz, 2 H), 2.09-2.03 (m, 1 H), 1.68-1.60 (m, 2 H), 1.51-1.40 (m, 2 H). |

Intermediate 7

4-Chloro-1-cyclopropyl-6-(4-fluorophenyl)phthalazine

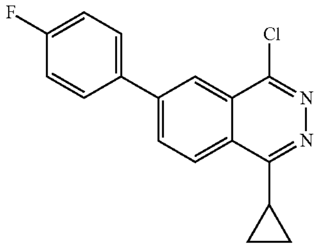 [SMILES: Fc1ccc(-c2ccc3c(C4CC4)nnc(Cl)c3c2)cc1]

Step 1) Preparation of 4-cyclopropyl-7-(4-fluorophenyl)phthalazin-1-ol

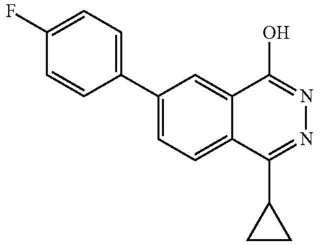

Nitrogen was bubbled for 10 minutes through a suspension of 7-bromo-4-cyclopropylphthalazin-1-ol (Intermediate 3) (250 mg, 0.943 mmol), 4-fluorophenyl boronic acid (158 mg, 1.13 mmol), potassium carbonate (391 mg, 2.83 mmol), Pd(dppf)Cl2 (34 mg, 0.047 mmol) in 1,4-dioxane (5 mL) and water (1 mL). The resulting mixture was stirred at 110° C. for 2 hours. The reaction mixture was cooled to RT. Water (10 mL) was added and the reaction was extracted with EtOAc (2×30 mL). The combined organic phases were passed through a hydrophobic frit and the solvent was removed in vacuo. The resulting residue was purified by chromatography on silica gel eluting with 0-10% MeOH in DCM to afford the title compound as a beige solid (231 mg, 87%).

LCMS (Method 2): [MH+]=281 at 4.64 min.

Step 2: Preparation of 4-chloro-1-cyclopropyl-6-(4-fluorophenyl)phthalazine

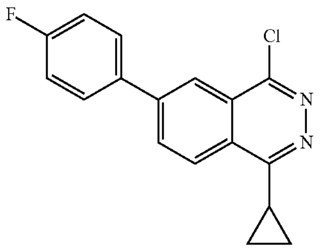 [SMILES: Fc1ccc(-c2ccc3c(C4CC4)nnc(Cl)c3c2)cc1]

A mixture of 4-cyclopropyl-7-(4-fluorophenyl)phthalazin-1-ol (110 mg, 0.392 mmol), phosphorus(V) oxychloride (1.8 mL, 18.95 mmol) and 1,2 dichloroethane (5 mL) was heated at 90° C. under nitrogen atmosphere for 2 hours. The reaction was cooled to RT and concentrated in vacuo. The residue was partitioned between water and DCM. The combined organic phases were washed with saturated aqueous sodium hydrogen carbonate solution, passed through a hydrophobic frit and the solvent was removed in vacuo to afford the title compound as a brown solid (116 mg, 99%).

LCMS (Method 2): [MH+]=299 at 5.59 min.

The following intermediates reported in the table below were prepared according to the procedure described for the preparation of 4-chloro-1-cyclopropyl-6-(4-fluorophenyl) phthalazine above.

| Intermediate No. | Chemical Name Structure | Analytical data $^1$H NMR LC-MS |
|---|---|---|
| Intermediate 8 | 4-Chloro-6-(4-fluorophenyl)-1-(tetrahydro-2H-pyran-4-yl)phthalazine 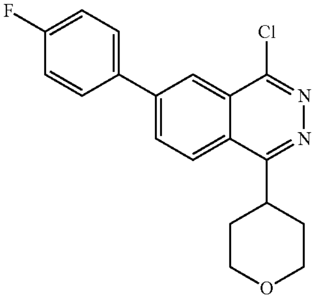 [SMILES: Fc1ccc(-c2ccc3c(C4CCOCC4)nnc(Cl)c3c2)cc1] | LCMS (Method 1): [MH+] = 343 at 5.08 min. |
| Intermediate 9 | 4-Chloro-6-(5-methylpyrimidin-2-yl)-1-(tetrahydro-2H-pyran-4-yl)phthalazine 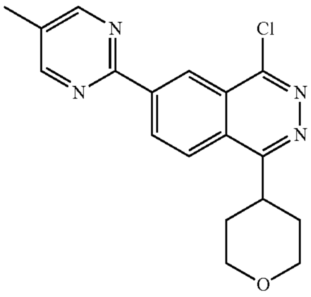 [SMILES: Cc1cnc(-c2ccc3c(C4CCOCC4)nnc(Cl)c3c2)nc1] | $^1$H NMR (400 MHz, $CDCl_3$): δ 9.41 (d, J = 1.4 Hz, 1 H), 9.02 (dd, J = 1.7, 8.7 Hz, 1 H), 8.75 (s, 2 H), 8.24 (d, J = 8.7 Hz, 1 H), 4.22-4.18 (m, 2 H), 3.81-3.68 (m, 3 H), 2.43 (s, 3 H), 2.42-2.30 (m, 2 H), 1.97 (dd, J = 1.4, 13.6 Hz, 2 H). |

Intermediate 10

2-(4-Chloro-1-((tetrahydro-2H-pyran-4-yl)methyl)phthalazin-6-yl)-5-methylthiazole

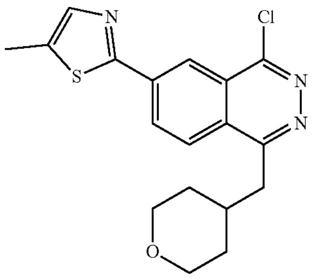 [SMILES: Cc1cnc(-c2ccc3c(CC4CCOCC4)nnc(Cl)c3c2)s1]

Step 1: Preparation of 7-(5-Methylthiazol-2-yl)-4-((tetrahydro-2H-pyran-4-yl)methyl)phthalazin-1-ol

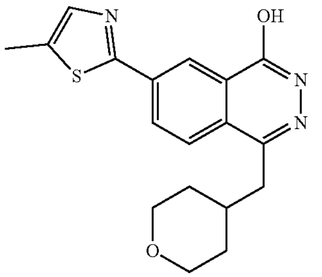

Nitrogen gas was bubbled through a mixture of 7-bromo-4-((tetrahydro-2H-pyran-4-yl)methyl)phthalazin-1-ol (Intermediate 5) (300 mg, 0.93 mmol), bis(neopentyl glycolato) diboron (283 mg, 1.11 mmol), Pd(dppf)$Cl_2$ (38 mg, 0.046 mmol) and potassium acetate (182 mg, 1.86 mmol) in dioxane (7.5 mL). The mixture was heated at 100° C. for 4 hours. The reaction mixture was cooled and taken on to the next step as a dioxane solution without further purification. Aqueous cesium carbonate solution (605 mg, 1.86 mmol) in water (1.5 mL) and 2-bromo-5-methylthiazole (174 mg, 0.98 mmol) were added. The resulting mixture was heated at 100° C. for an additional 18 hours. The reaction mixture was cooled, filtered through Celite® and the filter cake was washed with EtOAc (2×10 mL). The combined organic phases were passed through a hydrophobic frit and the solvent was removed in vacuo. The residue was purified by chromatography on silica gel eluting with 0-100% 9:1 EtOAc/EtOH in cyclohexane to afford the title compound as a beige solid (231 mg, 72% over 2 steps).

LCMS (Method 2): [MH+]=342 at 3.74 min.

Step 2: Preparation of 2-(4-Chloro-1-((tetrahydro-2H-pyran-4-yl)methyl)phthalazin-6-yl)-5-methylthiazole

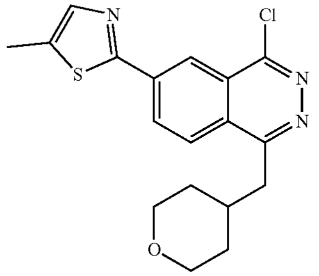 [SMILES: Cc1cnc(-c2ccc3c(CC4CCOCC4)nnc(Cl)c3c2)s1]

A mixture of 7-(5-methylthiazol-2-yl)-4-((tetrahydro-2H-pyran-4-yl)methyl)phthalazin-1-ol (231 mg, 0.68 mmol), phosphorus(V) oxychloride (3.0 mL, 32.5 mmol) and 1,2 dichloroethane (4 mL) was heated at 90° C. under nitrogen for 2 hours. The reaction mixture was cooled to RT and concentrated in vacuo. The resulting residue was partitioned between water and DCM. The combined organic phases were washed with saturated aqueous sodium hydrogen carbonate solution, passed through a hydrophobic frit and the solvent was removed in vacuo to afford the title compound as a pale brown solid (216 mg, 88%).

$^1$H NMR (400 MHz, $CDCl_3$): δ 8.73 (s, 1H), 8.54 (d, J=8.2 Hz, 1H), 8.15 (d, J=8.3 Hz, 1H), 7.69-7.63 (m, 1H), 3.96 (d, J=8.7 Hz, 2H), 3.42-3.26 (m, 4H), 2.60 (s, 3H), 2.28 (s, 1H), 1.70-1.54 (m, 3H), 1.28-1.19 (m, 1H).

Example 1

N-((6-Methylpyridazin-3-yl)methyl)-7-(5-methylpyrimidin-2-yl)-4-(tetrahydro-2H-pyran-4-yl)phthalazin-1-amine

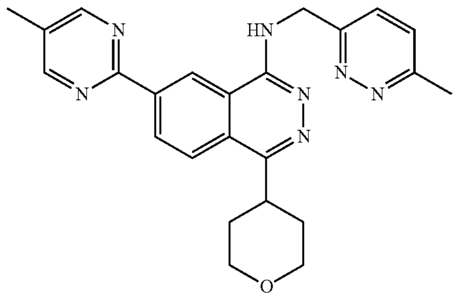

A mixture of 4-chloro-6-(5-methylpyrimidin-2-yl)-1-(tetrahydro-2H-pyran-4-yl)phthalazine (Intermediate 9) (50 mg, 0.13 mmol) and (6-methylpyridazin-3-yl)methanamine hydrochloride (49 mg, 0.40 mmol) in chloroform (0.5 mL) was heated in a sealed tube under nitrogen for 18 hours at 80° C. The mixture was cooled to RT, diluted with EtOAc (15 mL) and washed with a saturated aqueous sodium chloride solution. The organic phase was passed through a hydrophobic frit and the solvent was removed in vacuo. The resulting residue was purified by preparative HPLC to afford the title compound as an off-white solid (20.7 mg, 36%).

$^1$H NMR (400 MHz, DMSO): δ 9.36 (s, 1H), 8.89 (s, 2H), 8.84 (dd, J=1.4, 8.7 Hz, 1H), 8.49 (dd, J=5.8, 5.8 Hz, 1H), 8.33 (d, J=8.8 Hz, 1H), 7.56 (d, J=8.7 Hz, 1H), 7.48 (d, J=8.7 Hz, 1H), 5.02 (d, J=5.6 Hz, 2H), 3.99 (dd, J=2.6, 11.2 Hz, 2H), 3.71-3.59 (m, 3H), 2.60 (s, 3H), 2.39 (s, 3H), 2.00-1.88 (m, 2H), 1.81 (d, J=12.4 Hz, 2H). LCMS (Method 2): [MH+]=428 at 2.70 min.

Example 2

N-(Cyclopropylmethyl)-7-(4-fluorophenyl)phthalazin-1-amine

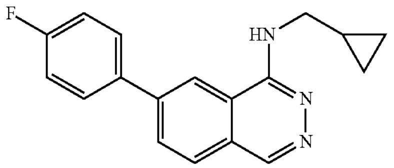 [SMILES: Fc1ccc(-c2ccc3cnnc(NCC4CC4)c3c2)cc1]

A mixture of 7-(4-fluorophenyl)phthalazin-1-ol (intermediate 3) (149 mg, 0.62 mmol) and phosphorous oxychloride (2.8 mL, 29.95 mmol) in 1,2-dichloroethane (5 mL) was heated at 90° C. for 1.5 h. The cooled mixture was diluted with DCM (20 mL), cooled in ice and treated with saturated $NaHCO_3$ (15 mL). The phases were separated, and the aqueous phase was extracted with DCM (2×10 mL). Combined organic phases were dried on $MgSO_4$ and the solvent removed in vacuo. The resultant brown solid triturated with $Et_2O$ (2×20 mL) and dried to afford a yellow coloured solid (160 mg). 63 mg of this solid was treated with cyclopropylmethylamine (1 mL, 11.67 mmol) and heated at 80° C. in a capped microwave vial for 5 h. The solvent was removed in vacuo and the residue purified by preparative HPLC to afford N-(cyclopropylmethyl)-7-(4-fluorophenyl)phthalazin-1-amine as an off white solid (34.7 mg, 49%).

$^1H$ NMR (400 MHz, DMSO): δ 8.78-8.77 (m, 1H), 8.50-8.48 (m, 1H), 8.06 (dd, J=1.7, 8.3 Hz, 1H), 7.87-7.80 (m, 3H), 7.58-7.53 (m, 1H), 7.31-7.26 (m, 2H), 3.35-3.31 (m, 2H), 1.22-1.11 (m, 1H), 0.40-0.34 (m, 2H), 0.21-0.16 (m, 2H). LCMS (Method 1): [MH+]=294 at 4.70 min.

The following compound was obtained using the same procedure used for the preparation of N-(cyclopropylmethyl)-7-(4-fluorophenyl)phthalazin-1-amine.

| Example No. | Chemical Name Structure | Analytical data $^1H$ NMR LC-MS |
|---|---|---|
| Example 3 | 7-(4-Fluorophenyl)-N-((6-methylpyridazin-3-yl)methyl)phthalazin-1-amine 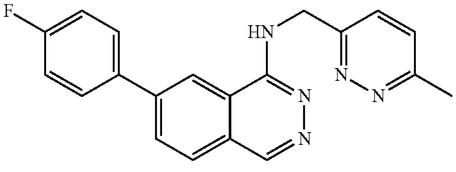 [SMILES: Cc1ccc(CNc2nncc3ccc(-c4ccc(F)cc4)cc23)nn1] | $^1H$ NMR (400 MHz, DMSO): δ 8.97 (s, 1 H), 8.70 (s, 1 H), 8.40 (t, J = 5.9 Hz, 1 H), 8.25 (dd, J = 1.7, 8.3 Hz, 1 H), 8.06-7.95 (m, 3 H), 7.61-7.58 (m, 1 H), 7.50-7.40 (m, 3 H), 5.08-5.05 (m, 2 H), 2.60 (s, 3 H). LCMS (Method 1): [MH+] = 346 at 3.77 min. |

Example 4

(R)-4-Cyclopropyl-7-(4-fluorophenyl)-N-(1-(2-(trifluoromethyl)pyrimidin-5-yl)ethyl)phthalazin-1-amine

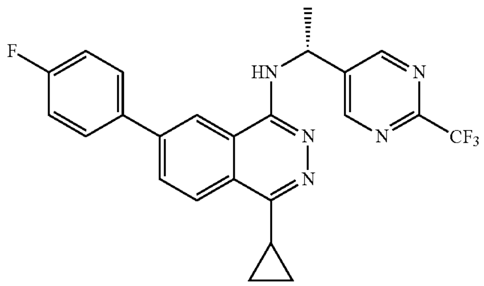 [SMILES: C[C@@H](Nc1nnc(C2CC2)c2ccc(-c3ccc(F)cc3)cc12)c1cnc(C(F)(F)F)nc1]

A mixture of 4-chloro-1-cyclopropyl-6-(4-fluorophenyl)phthalazine (Intermediate 7) (55 mg, 0.18 mmol) and (R)-1-(2-(trifluoromethyl)pyrimidin-5-yl)ethan-1-amine (105 mg, 0.55 mmol) was heated in a sealed tube under nitrogen for 6 hours at 80° C. The resulting reaction was cooled to RT, diluted with EtOAc (15 mL), washed with saturated aqueous sodium chloride solution. The organic phase was collected, passed through a hydrophobic frit and the solvent was removed in vacuo. The resulting residue was purified by preparative HPLC to afford the title compound as an off-white solid (23.7 mg, 28%).

$^1H$ NMR (400 MHz, DMSO): δ 9.15 (s, 2H), 8.72 (d, J=1.5 Hz, 1H), 8.41 (d, J=8.5 Hz, 1H), 8.26 (dd, J=1.7, 8.6 Hz, 1H), 8.02-7.98 (m, 2H), 7.85 (d, J=6.4 Hz, 1H), 7.45 (dd, J=8.8, 8.8 Hz, 2H), 5.58-5.52 (m, 1H), 2.63-2.55 (m, 1H), 1.74 (d, J=7.2 Hz, 3H), 1.03-0.96 (m, 4H). LCMS (Method 1): [MH+]=454 at 5.51 min.

The following compound reported in the table below were prepared according to the procedure described for the preparation of (R)-4-cyclopropyl-7-(4-fluorophenyl)-N-(1-(2-(trifluoromethyl)pyrimidin-5-yl)ethyl)phthalazin-1-amine above.

| Example No. | Chemical Name<br>Structure | Analytical data<br>$^1$H NMR<br>LC-MS |
|---|---|---|
| Example 5 | (R)-4-Cyclopropyl-7-(4-fluorophenyl)-N-(1-(6-methylpyridazin-3-yl)ethyl)phthalazin-1-amine<br>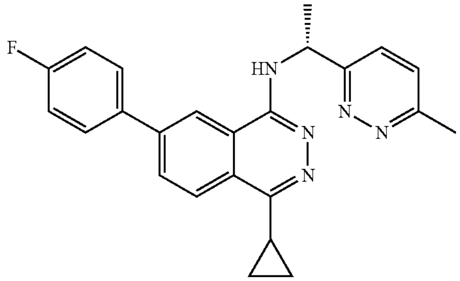 [SMILES: Cc1ccc([C@@H](C)Nc2nnc(C3CC3)c3ccc(-c4ccc(F)cc4)cc23)nn1] | $^1$H NMR (400 MHz, DMSO): δ 8.80 (d, J = 1.6 Hz, 1 H), 8.39 (d, J = 8.7 Hz, 1 H), 8.26 (dd, J = 1.8, 8.7 Hz, 1 H), 8.04-8.00 (m, 2 H), 7.85 (d, J = 7.0 Hz, 1 H), 7.58 (d, J = 8.7 Hz, 1 H), 7.47-7.42 (m, 3 H), 5.70-5.61 (m, 1 H), 2.58 (s, 3 H), 2.56-2.55 (m, 1 H), 1.71 (d, J = 7.0 Hz, 3 H), 1.00-0.95 (m, 4 H). LCMS (Method 1): [MH+] = 400 at 4.62 min. |
| Example 6 | (R)-7-(4-Fluorophenyl)-4-(tetrahydro-2H-pyran-4-yl)-N-(1-(2-(trifluoromethyl)pyrimidin-5-yl)ethyl)phthalazin-1-amine<br>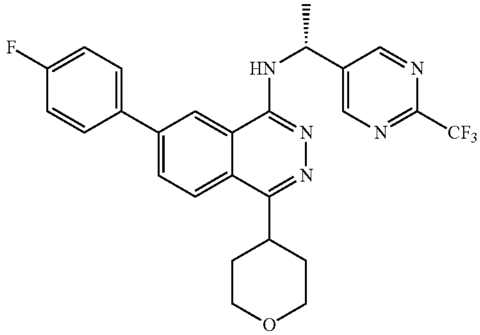 [SMILES: C[C@@H](Nc1nnc(C2CCOCC2)c2ccc(-c3ccc(F)cc3)cc12)c1cnc(C(F)(F)F)nc1] | $^1$H NMR (400 MHz, DMSO): δ 9.18 (s, 2 H), 8.74 (d, J = 1.5 Hz, 1 H), 8.27 (d, J = 8.8 Hz, 1 H), 8.24-8.20 (m, 1 H), 8.01-7.96 (m, 2 H), 7.90 (d, J = 6.4 Hz, 1 H), 7.45 (dd, J = 8.9, 8.9 Hz, 2 H), 5.63-5.58 (m, 1 H), 3.97 (dd, J = 2.1, 9.2 Hz, 2 H), 3.69-3.57 (m, 3 H), 1.98-1.85 (m, 2 H), 1.82-1.77 (m, 2 H), 1.75 (d, J = 7.2 Hz, 3 H). LCMS (Method 1): [MH+] = 498 at 5.26 min. Chiral analysis (Method 3) at 2.52 min. |
| Example 7 | (R)-7-(4-Fluorophenyl)-N-(1-(6-methylpyridazin-3-yl)ethyl)-4-(tetrahydro-2H-pyran-4-yl)phthalazin-1-amine<br>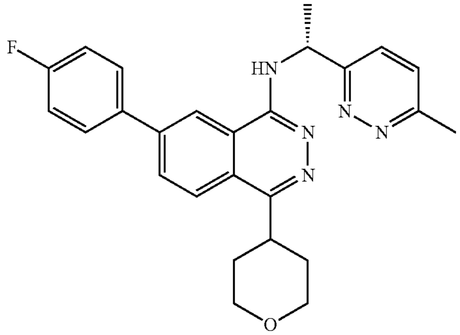 [SMILES: Cc1ccc([C@@H](C)Nc2nnc(C3CCOCC3)c3ccc(-c4ccc(F)cc4)cc23)nn1] | $^1$H NMR (400 MHz, DMSO): δ 8.82 (s, 1 H), 8.27-8.20 (m, 2 H), 8.03-7.99 (m, 2 H), 7.90 (d, J = 7.2 Hz, 1 H), 7.62 (d, J = 8.7 Hz, 1 H), 7.49-7.41 (m, 3 H), 5.75-5.66 (m, 1 H), 3.97 (dd, J = 2.0, 9.2 Hz, 2 H), 3.68-3.57 (m, 3 H), 2.59 (s, 3 H), 1.98-1.86 (m, 2 H), 1.79-1.75 (m, 2 H), 1.72 (d, J = 7.0 Hz, 3 H). LCMS (Method 1): [MH+] = 444 at 4.57 min. Chiral analysis (Method 6) at 3.62 min. |

Intermediate 11

7-(5-Fluoro-2-pyridyl)-N-[(3-methyl-1,2,4-oxadiazol-5-yl)methyl]-4-tetrahydropyran-4-yl-phthalazin-1-amine

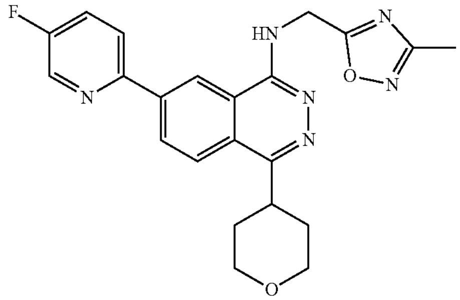 [SMILES: Cc1noc(CNc2nnc(C3CCOCC3)c3ccc(-c4ccc(F)cn4)cc23)n1]

Step 1: Preparation of 7-(5-fluoropyridin-2-yl)-4-(tetrahydro-2H-pyran-4-yl)phthalazin-1-ol

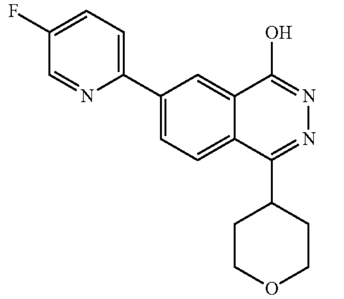 [SMILES: Oc1nnc(C2CCOCC2)c2ccc(-c3ccc(F)cn3)cc12]

Nitrogen gas was bubbled for 10 minutes through a mixture of 7-bromo-4-(tetrahydro-2H-pyran-4-yl)phthalazin-1-ol (intermediate 5) (500 mg, 1.62 mmol), bis(neopentyl glycolato) diboron (493 mg, 1.94 mmol), Pd(dppf)$Cl_2$ (66 mg, 0.081 mmol) and potassium acetate (317 mg, 3.23 mmol) in dioxane (12.5 mL). The mixture was heated at 100° C. for 4 hours. The reaction mixture was cooled and taken on to the next step as a dioxane solution without further purification. To this solution was added aqueous cesium carbonate (1054 mg, 3.23 mmol, 2.5 mL) and 2-bromo-5-fluoropyridine (299 mg, 1.70 mmol). The resulting mixture was heated at 100° C. for 18 hours. The reaction was cooled, filtered through Celite® and the filter cake washed with EtOAc (2×10 mL). The organic phases were combined, passed through a hydrophobic frit and the solvent was removed in vacuo. The residue was purified by chromatography on silica gel eluting with 3-70% 3:1 EtOAc/EtOH in cyclohexane to afford the title compound as a pale orange solid (380 mg, 72% over 2 steps).

$^1$H NMR (400 MHz, $CDCl_3$): δ 9.96 (s, 1H), 8.95 (d, J=2.0 Hz, 1H), 8.63-8.60 (m, 2H), 8.00-7.95 (m, 2H), 7.59-7.52 (m, 1H), 4.17-4.10 (m, 2H), 3.70-3.62 (m, 2H), 3.45-3.36 (m, 1H), 2.10-1.98 (m, 2H), 1.90 (dd, J=1.6, 13.5 Hz, 2H).

Step 2: Preparation of 4-Chloro-6-(5-fluoropyridin-2-yl)-1-(tetrahydro-2H-pyran-4-yl)phthalazine

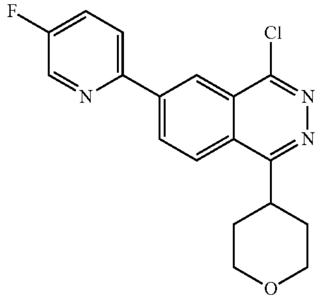 [SMILES: Fc1ccc(-c2ccc3c(C4CCOCC4)nnc(Cl)c3c2)nc1]

A mixture of 7-(5-fluoropyridin-2-yl)-4-(tetrahydro-2H-pyran-4-yl)phthalazin-1-ol (380 mg, 1.18 mmol), phosphorus(V) oxychloride (5.3 mL, 56.7 mmol) and 1,2 dichloroethane (10 mL) was heated at 90° C. under nitrogen for 2 hours. The reaction was cooled to RT and the solvent was removed in vacuo. The residue was partitioned between water and DCM. The aqueous phase was extracted with dichloromethane (2×20 mL). The organic phases were combined, washed with an aqueous saturated sodium hydrogen carbonate solution, passed through a hydrophobic frit. The solvent was removed in vacuo to give the title compound (370 mg, 91%) as a pale brown solid, which was taken on to the next step without further purification.

Step 3: Preparation of 7-(5-Fluoro-2-pyridyl)-N-[(3-methyl-1,2,4-oxadiazol-5-yl)methyl]-4-tetrahydropyran-4-yl-phthalazin-1-amine

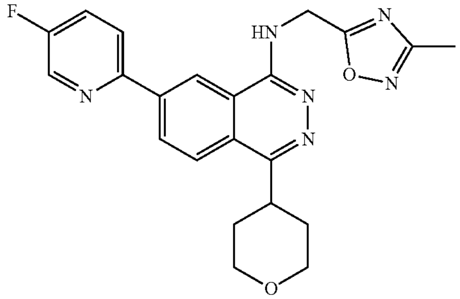 [SMILES: Cc1noc(CNc2nnc(C3CCOCC3)c3ccc(-c4ccc(F)cn4)cc23)n1]

A mixture of 4-Chloro-6-(5-fluoropyridin-2-yl)-1-(tetrahydro-2H-pyran-4-yl)phthalazine (50 mg, 0.13 mmol), 3-methyl-1,2,4-oxadiazol-5-yl)methanamine·hydrochloride (59 mg, 0.40 mmol) in chloroform (0.5 mL) and $Et_3N$ (0.07 mL, 0.52 mmol) were heated in a sealed tube under nitrogen for 18 hours at 80° C.

The resulting mixture was cooled to RT, diluted with EtOAc (15 mL) and washed with saturated aqueous sodium chloride. The organic phases were passed through a hydrophobic frit and the solvent was removed in vacuo. The resulting residue was purified by preparative HPLC to afford the title compound as an off-white solid (22.0 mg, 22%).

$^1$H NMR (400 MHz, DMSO): δ 9.03 (d, J=1.5 Hz, 1H), 8.80 (d, J=2.9 Hz, 1H), 8.64 (dd, J=1.6, 8.7 Hz, 1H), 8.47

(dd, J=5.6, 5.6 Hz, 1H), 8.37-8.32 (m, 2H), 8.06-8.00 (m, 1H), 5.01 (d, J=5.6 Hz, 2H), 3.99 (dd, J=2.7, 11.4 Hz, 2H), 3.73-3.58 (m, 3H), 2.32 (s, 3H), 2.01-1.89 (m, 2H), 1.80 (d, J=14.1 Hz, 2H). LCMS (Method 2): [MH+]=421 at 3.00 min.

The following compounds reported in the table below were prepared according to the procedure described for the preparation of 7-(5-Fluoro-2-pyridyl)-N-[(3-methyl-1,2,4-oxadiazol-5-yl)methyl]-4-tetrahydropyran-4-yl-phthalazin-1-amine:

| Example No. | Chemical Name<br>Structure | Analytical data<br>$^1$H NMR<br>LC-MS |
|---|---|---|
| Example 9 | 7-(5-Fluoropyridin-2-yl)-N-((6-methylpyridazin-3-yl)methyl)-4-(tetrahydro-2H-pyran-4-yl)phthalazin-1-amine<br>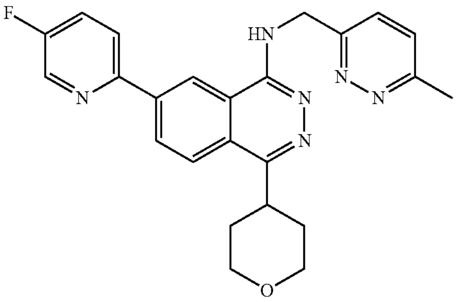 [SMILES: Cc1ccc(CNc2nnc(C3CCOCC3)c3ccc(-c4ccc(F)cn4)cc23)nn1] | $^1$H NMR (400 MHz, DMSO): δ 9.04 (d, J = 1.5 Hz, 1 H), 8.78 (d, J = 3.0 Hz, 1 H), 8.62 (dd, J = 1.6, 8.7 Hz, 1 H), 8.38-8.29 (m, 3 H), 8.04-7.98 (m, 1 H), 7.59 (d, J = 8.7 Hz, 1 H), 7.49 (d, J = 8.7 Hz, 1 H), 5.04 (d, J = 5.6 Hz, 2 H), 4.02-3.96 (m, 2 H), 3.71-3.58 (m, 3 H), 2.61 (s, 3 H), 2.01-1.89 (m, 2 H), 1.82-1.77 (m, 2 H). LCMS (Method 2): [MH$^+$] = 431 at 2.81 min. |
| Example 10 | 7-(5-Fluoropyridin-2-yl)-N-((6-methylpyridazin-3-yl)methyl)-4-((tetrahydro-2H-pyran-4-yl)methyl)phthalazin-1-amine<br>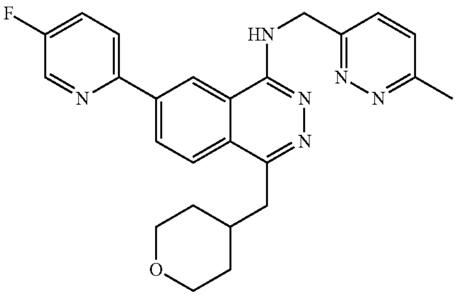 [SMILES: Cc1ccc(CNc2nnc(CC3CCOCC3)c3ccc(-c4ccc(F)cn4)cc23)nn1] | H NMR (400 MHz, DMSO): δ 9.03 (d, J = 1.5 Hz, 1 H), 8.78 (d, J = 3.0 Hz, 1 H), 8.61 (dd, J = 1.6, 8.7 Hz, 1 H), 8.36-8.30 (m, 2 H), 8.22 (d, J = 8.7 Hz, 1 H), 8.04-7.98 (m, 1 H), 7.59 (d, J = 8.7 Hz, 1 H), 7.49 (d, J = 8.8 Hz, 1 H), 5.04 (d, J = 5.6 Hz, 2 H), 3.82 (dd, J = 2.5, 11.4 Hz, 2 H), 3.27-3.20 (m, 2 H), 3.04 (d, J = 7.0 Hz, 2 H), 2.60 (s, 3 H), 2.11-2.01 (m, 1 H), 1.55 (dd, J = 1.7, 12.9 Hz, 2 H), 1.40-1.27 (m, 2 H). LCMS (Method 2): [MH$^+$] = 445 at 2.80 min. |

The following compounds reported in the table below were prepared according to the procedure described for the preparation of 7-(5-Fluoro-2-pyridyl)-N-[(3-methyl-1,2,4-oxadiazol-5-yl)methyl]-4-tetrahydropyran-4-yl-phthalazin-1-amine. The single isomers were obtained by chiral preparative SFC purification of the corresponding racemic mixture.

| Example No. | Chemical Name<br>Structure | Analytical data<br>$^1$H NMR<br>LC-MS |
|---|---|---|
| Example 11 | Single enantiomer 1 of 7-(5-Fluoropyridin-2-yl)-N-(1-(6-methylpyridazin-3-yl)ethyl)-4-(tetrahydro-2H-pyran-4-yl)phthalazin-1-amine<br>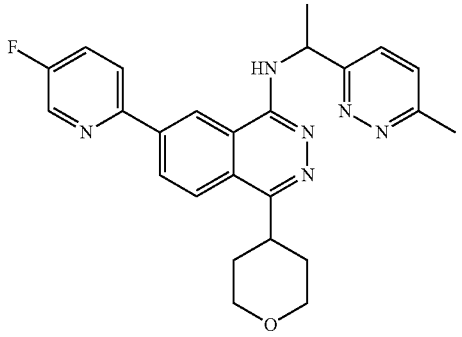 [SMILES: Cc1ccc(C(C)Nc2nnc(C3CCOCC3)c3ccc(-c4ccc(F)cn4)cc23)nn1] | $^1$H NMR (400 MHz, DMSO): δ 9.13 (d, J = 1.5 Hz, 1 H), 8.80 (d, J = 2.9 Hz, 1 H), 8.62 (dd, J = 1.6, 8.7 Hz, 1 H), 8.41 (dd, J = 4.4, 8.9 Hz, 1 H), 8.29 (d, J = 8.9 Hz, 1 H), 8.05-7.96 (m, 2 H), 7.63 (d, J = 8.5 Hz, 1 H), 7.48 (d, J = 8.7 Hz, 1 H), 5.74-5.69 (m, 1 H), 3.99-3.96 (m, 2 H), 3.68-3.57 (m, 3 H), 2.59 (s, 3 H), 1.98-1.85 (m, 2 H), 1.80-1.76 (m, 2 H), 1.74 (d, J = 7.2 Hz, 3 H). LCMS (Method 2): [MH$^+$] = 445 at 3.02 min. Chiral analysis (Method 4) at 1.32 min. |

Example 13

N-[(6-Methylpyridazin-3-yl)methyl]-7-(5-methylthiazol-2-yl)phthalazin-1-amine

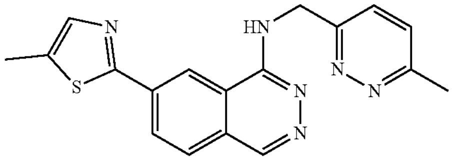

Step 1: Preparation of 7-(5-methylthiazol-2-yl)phthalazin-1-ol

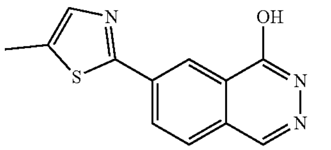

Nitrogen gas was bubbled for 5 minutes through a mixture of 7-bromo-phthalazin-1-ol (113 mg, 0.502 mmol) (Intermediate 2) and 5-methyl-2-(tributylstannyl)thiazole (195 mg, 0.502 mmol) in anhydrous 1,4-dioxane (2 mL) and anhydrous toluene (2 mL). Tetrakis(triphenylphosphine) palladium (0 (29 mg, 0.0251 mmol) was added. The mixture was heated in microwave reactor at 150° C. for 3 hours, cooled, diluted with DCM and the solvent was removed in vacuo. The residue was purified by chromatography on silica gel eluting with 0-20% MeOH in DCM to afford the title compound as a colourless solid (110 mg, 90%).

LCMS (Method 1): [MH+]=244 at 3.28 min.

Step 2: Preparation of N-[(6-methylpyridazin-3-yl)methyl]-7-(5-methylthiazol-2-yl)phthalazin-1-amine

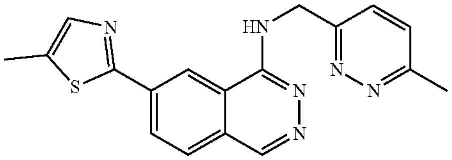

A mixture of 7-(5-methylthiazol-2-yl)phthalazin-1-ol (110 mg, 0.452 mmol) and phosphorus(V) oxychloride (2 mL) in 1,2-dichloroethane (5 mL) was heated at 90° C. for 2 hours. The mixture was cooled, diluted with DCM (30 mL) and washed with cold saturated sodium hydrogen carbonate (10 mL). The organic phase was separated, and the aqueous layer extracted with DCM (10 mL). The combined organic phases were dried on $MgSO_4$, filtered and the solvent was removed in vacuo. The residue was added to (6-methylpyridazin-3-yl)methanamine and the mixture was heated at 90° C. for 2 hours and then allowed to cool. The solvent was removed in vacuo and the residue was purified by reverse phase preparative HPLC to afford the title compound as a pale brown solid (4.1 mg, 2.6%).

$^1$H NMR (400 MHz, DMSO): δ 8.97-8.96 (m, 1H), 8.88 (s, 1H), 8.60 (t, J=5.8 Hz, 1H), 8.42-8.35 (m, 1H), 8.06-8.03 (m, 1H), 7.77-7.75 (m, 1H), 7.60-7.57 (m, 1H), 7.50-7.47 (m, 1H), 5.04 (d, J=5.6 Hz, 2H), 2.60 (s, 3H), 2.58 (d, J=1.1 Hz, 3H).

LCMS (Method 1): [MH+]=349 at 3.33 min.

Example 14

7-(5-Methylthiazol-2-yl)-4-((tetrahydro-2H-pyran-4-yl)methyl)-N-((3-(trifluoromethyl)-1,2,4-oxadiazol-5-yl)methyl)phthalazin-1-amine

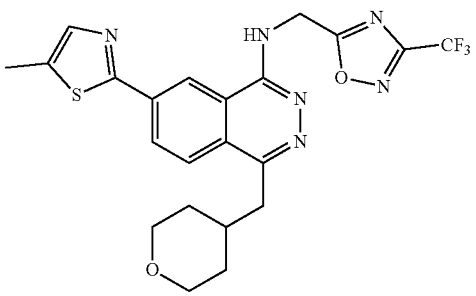 [SMILES: Cc1cnc(-c2ccc3c(CC4CCOCC4)nnc(NCc4nc(C(F)(F)F)no4)c3c2)s1]

2-(4-Chloro-1-((tetrahydro-2H-pyran-4-yl)methyl)phthalazin-6-yl)-5-methylthiazole (52 mg, 0.13 mmol) (Intermediate 10) and (3-(trifluoromethyl)-1,2,4-oxadiazol-5-yl)methanamine hydrochloride (32 mg, 0.16 mmol) in DIPEA (0.06 mL, 0.33 mmol) and 1,4-dioxane (0.5 mL) were heated in a microwave reactor at 100° C. for 1.5 hours. The resulting mixture was cooled to RT, diluted with EtOAc (15 mL) and washed with a saturated aqueous sodium chloride solution. The organic phases were passed through a hydrophobic frit and the solvent was removed in vacuo. The resulting residue was purified by preparative HPLC to afford the title compound as an off white solid (3.91 mg, 6%).

$^1$H NMR (400 MHz, DMSO): δ 8.85 (d, J=1.6 Hz, 1H), 8.72 (dd, J=5.6, 5.6 Hz, 1H), 8.43 (dd, J=1.8, 8.7 Hz, 1H), 8.26 (d, J=8.8 Hz, 1H), 7.79 (d, J=1.3 Hz, 1H), 5.13 (d, J=5.5 Hz, 2H), 3.81 (dd, J=2.8, 11.3 Hz, 2H), 3.23 (dd, J=9.9, 11.5 Hz, 2H), 3.04 (d, J=7.2 Hz, 2H), 2.59 (s, 3H), 2.06-2.00 (m, 1H), 1.53-1.48 (m, 2H), 1.38-1.27 (m, 2H). LCMS (Method 1): [MH+]=491 at 4.71 min.

The following compound reported in the table below was prepared according to the procedure described for the preparation of 7-(5-Methylthiazol-2-yl)-4-((tetrahydro-2H-pyran-4-yl)methyl)-N-((3-(trifluoromethyl)-1,2,4-oxadiazol-5-yl)methyl)phthalazin-1-amine.

| Example No. | Chemical Name<br>Structure | Analytical data<br>$^1$H NMR<br>LC-MS |
|---|---|---|
| Example 15 | N-((6-Methylpyridazin-3-yl)methyl)-7-(5-methylthiazol-2-yl)-4-((tetrahydro-2H-pyran-4-yl)methyl)phthalazin-1-amine<br>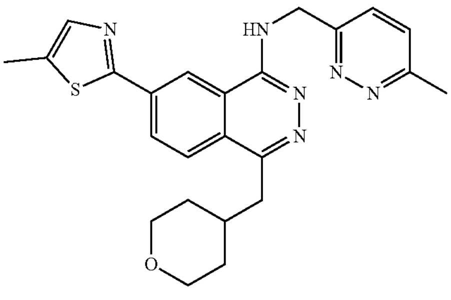 | $^1$H NMR (400 MHz, DMSO): δ 8.85 (d, J = 1.5 Hz, 1 H), 8.45 (dd, J = 5.8, 5.8 Hz, 1 H), 8.41-8.38 (m, 1 H), 8.20 (d, J = 8.7 Hz, 1 H), 7.76 (d, J = 1.1 Hz, 1 H), 7.57 (d, J = 8.7 Hz, 1 H), 7.48 (d, J = 8.7 Hz, 1 H), 5.01 (d, J = 5.8 Hz, 2 H), 3.81 (dd, J = 2.6, 11.4 Hz, 2 H), 3.26-3.19 (m, 2 H), 3.02 (d, J = 7.2 Hz, 2 H), 2.59 (s, 3 H), 2.57 (s, 3 H), 2.09-1.99 (m, 1 H), 1.54 (d, J = 11.0 Hz, 2 H), 1.38-1.26 (m, 2 H). LCMS (Method 2): [MH$^+$] = 447 at 2.81 min. |

Example 16

4-Cyclopropyl-7-(1-methyl-1H-pyrazol-3-yl)-N-(1-(6-methylpyridazin-3-yl)ethyl)phthalazin-1-amine

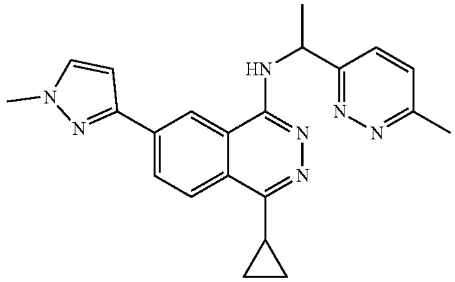

Step 1: Preparation of 4-cyclopropyl-7-(1-methyl-1H-pyrazol-3-yl)phthalazin-1-ol

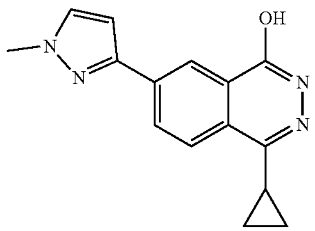 [SMILES: Cn1ccc(-c2ccc3c(C4CC4)nnc(O)c3c2)n1]

Nitrogen was bubbled for 10 minutes through a suspension of 7-bromo-4-cyclopropylphthalazin-1-ol (Intermediate 4) (120 mg, 0.45 mmol), 1-methyl-3-(4,4,5,5-tetramethyl-1,3,2-dioxaborolan-2-yl)-1H-pyrazole (122 mg, 0.59 mmol), cesium carbonate (295 mg, 0.91 mmol), $Pd(dppf)Cl_2$ (33 mg, 0.045 mmol) in 1,4-dioxane (4 mL) and water (1 mL). The resulting mixture was stirred at 90° C. for 2 hours. The reaction mixture was cooled to RT. The reaction was partitioned between water (10 mL) and EtOAc (30 mL). The aqueous layer was extracted with EtOAc (2×30 mL). The organic phases were combined, passed through a hydrophobic frit and the solvent was removed in vacuo. The resulting residue was purified by chromatography on silica gel eluting with 0-6% MeOH in DCM to afford the title compound as a beige solid (117 mg, 96%).

LCMS (Method 2): [MH+]=267 at 3.62 min

Step 2: Preparation of 4-chloro-1-cyclopropyl-6-(1-methyl-1H-pyrazol-3-yl)phthalazine

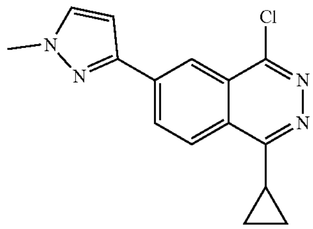 [SMILES: Cn1ccc(-c2ccc3c(C4CC4)nnc(Cl)c3c2)n1]

A mixture of 4-cyclopropyl-7-(1-methyl-1H-pyrazol-3-yl)phthalazin-1-ol (110 mg, 0.41 mmol), phosphorus(V) oxychloride (1.9 mL, 20.0 mmol) and 1,2 dichloroethane (5 mL) was heated at 90° C. under nitrogen for 4 hours. The reaction was cooled to RT and concentrated in vacuo. The residue was then partitioned between water and DCM. The aqueous layer was extracted with DCM (2×30 mL). The combined organic phases were washed with a saturated aqueous sodium hydrogen carbonate solution, passed through a hydrophobic frit and the solvent was removed in vacuo to afford the title compound as a brown solid (116 mg, 99%).

LCMS (Method 2): [MH+]=285 at 4.33 min.

Step 3: Preparation of 4-cyclopropyl-7-(1-methyl-1H-pyrazol-3-yl)-N-(1-(6-methyl pyridazin-3-yl) ethyl)phthalazin-1-amine

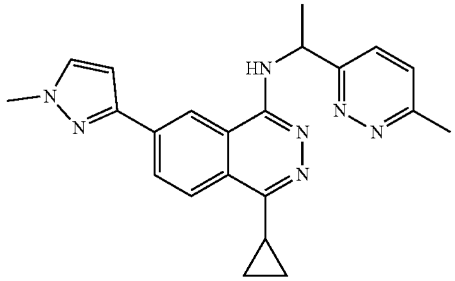

A mixture of 4-chloro-1-cyclopropyl-6-(1-methyl-1H-pyrazol-3-yl)phthalazine (113 mg, 0.36 mmol) and neat 1-(6-methylpyridazin-3-yl)ethan-1-amine hydrochloride (147 mg, 1.07 mmol) was heated in a sealed tube under nitrogen for 4 days at 80° C. The resulting residue was cooled to RT, diluted with EtOAc (15 mL), washed with saturated aqueous sodium chloride solution. The organic phase was passed through a hydrophobic frit and the solvent was removed in vacuo. The resulting residue was purified by preparative HPLC to afford the title compound as an off-white solid (25.1 mg, 28%).

$^1$H NMR (400 MHz, DMSO): δ 8.82 (s, 1H), 8.37-8.31 (m, 2H), 7.80 (d, J=2.3 Hz, 1H), 7.59 (d, J=8.7 Hz, 1H), 7.44 (d, J=8.8 Hz, 1H), 7.02 (d, J=2.3 Hz, 1H), 5.65-5.62 (m, 1H), 3.97 (s, 2H), 2.55 (s, 3H), 2.54-2.51 (m, 1H), 1.7 (d, J=7.0 Hz, 3H), 0.96-0.92 (m, 4H). LCMS (Method 2): [MH+]=386 at 2.78 min.

The following compound reported in the table below was prepared according to the procedure described for the preparation of 4-cyclopropyl-7-(1-methyl-1H-pyrazol-3-yl)-N-(1-(6-methyl pyridazin-3-yl)ethyl)phthalazin-1-amine.

| Example No. | Chemical Name<br>Structure | Analytical data<br>$^1$H NMR<br>LC-MS |
|---|---|---|
| Example 17 | 7-(1-Methylpyrazol-3-yl)-N-[1-(6-methylpyridazin-3-yl)ethyl]-4-tetrahydropyran-4-yl-phthalazin-1-amine<br>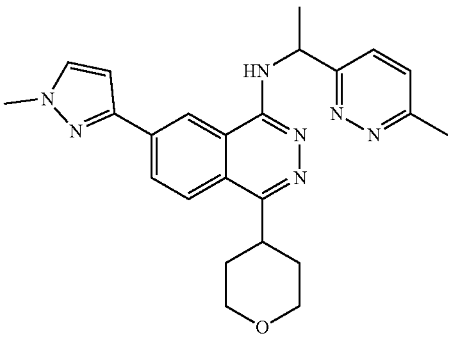 | $^1$H NMR (400 MHz, DMSO): δ 8.84 (d, J = 1.6 Hz, 1 H), 8.35-8.33 (m, 1 H), 8.19 (d, J = 8.8 Hz, 1 H), 7.88-7.84 (m, 2 H), 7.63 (d, J = 8.4 Hz, 1 H), 7.47 (d, J = 8.4 Hz, 1 H), 7.03 (d, J = 2.4 Hz, 1 H), 5.70-5.67 (m, 1 H), 3.97-3.63 (m, 4 H), 3.62-3.59 (m, 4 H), 2.58 (s, 3 H), 1.92-1.89 (m, 2 H), 1.86-1.85 (m, 2 H), 1.75-1.71 (m, 3 H). LCMS (Method 2): [MH$^+$] = 430 at 2.67 min. |

The following compound reported in the table below were obtained as single isomers by chiral preparative SFC purification of the racemic mixture hereinabove described.

| Example No. | Chemical Name Structure | Analytical data $^1H$ NMR LC-MS |
|---|---|---|
| Example 19 | Single enatiomer 2 of 4-Cyclopropyl-7-(1-methyl-1/-pyrazol-3-yl)-N-(1-(6-methylpyridazin-3-yl)ethyl)phthalazin-1-amine 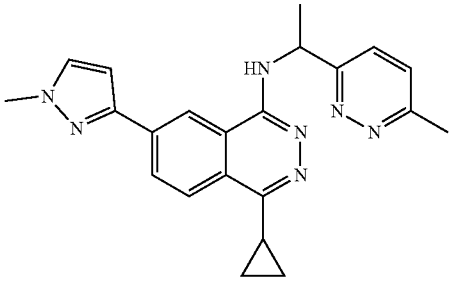 | $^1H$ NMR (400 MHz, DMSO): δ 8.78 (s, 1 H), 8.39-8.34 (m, 2 H), 7.82 (d, J = 2.3 Hz, 1 H), 7.60 (d, J = 8.7 Hz, 1 H), 7.46 (d, J = 8.8 Hz, 1 H), 7.01 (d, J = 2.3 Hz, 1 H), 5.56 (q, J = 7.2 Hz, 1 H), 3.94 (s, 2 H), 2.55 (s, 3 H), 2.50-2.45 (m, 1 H), 1.67 (d, J = 7.0 Hz, 3 H), 0.98-0.90 (m, 4 H). LCMS (Method 2): [MH+] = 386 at 2.74 min. Chiral analysis (Method 7) at 3.55 min. |

Pharmacological Activity of the Compounds of the Invention.

In Vitro Electrophysiology Assay for $P2X_3$

Cells expressing $P2X_3$ receptors were grown according to standard practice and maintained at 37° C. in a 5% humidified $CO_2$ atmosphere. The cells were seeded into T175 flask 2 days prior to the day of the assay and dissociated from the flasks using TrypLE when grown to confluence of 80-90%. The dissociated cells were resuspended in serum free media at a cell density of $3\times10^6$ cells/ml and loaded onto the Sophion Qube automated patch-clamp system. The extracellular assay buffer contained 145 mM NaCl, 4 mM KCl, 2 mM $CaCl_2$, 1 mM $MgCl_2$, 10 mM HEPES, and 10 mM glucose at pH 7.4. The intracellular assay solution contained 140 mM CsF, 10 mM NaCl, 10 mM EGTA, 10 mM HEPES at pH 7.2. Agonist stock solutions were prepared in $H_2O$ and diluted in bath solution prior to use. All antagonists were prepared as 10 mM stock solutions in DMSO and diluted in bath solution prior to use. All experiments were performed under the whole-cell patch clamp configuration at room temperature with 384 individual cells being voltage clamped at −60 mV simultaneously on the Sophion Qube instrument. Two baseline responses were established with the application of α,β-MeATP (800 nM), with the subsequent agonist applications being washed out using extracellular assay buffer containing 0.5 U/ml apyrase. Following the second agonist application, antagonist was incubated in the absence of α,β-MeATP for 10 minutes. After antagonist preincubation, 800 nM α,β-MeATP and antagonist were co-administered to determine the inhibitory effect of the antagonist. One concentration of an antagonist was assessed against a single cell, with different concentrations of the antagonist applied to other cells on the 384 recording substrate. The control $P2X_3$ current amplitude was taken from the peak current amplitude from the second agonist response prior to preincubation with antagonist. The peak $P2X_3$ current amplitude in the presence of antagonist was used to calculate the inhibitory effect at each concentration of the antagonist according to the following equation:

$$\text{Percentage inhibition of } P2X_3=(P2X_3 \text{ control peak amplitude-}P2X_3 \text{ antagonist peak amplitude})/P2X_3 \text{ control peak amplitude})*100$$

Concentration-response curves were constructed from ten different concentrations with each concentration of antagonist tested on at least two individual cells. The concentration of the antagonist to inhibit $P2X_3$ current by 50% ($IC_{50}$) was determined by fitting the data with the following equation:

$$Y=a+[(b-a)/(1+10^{\wedge}((\log c-x)d)]$$

Where 'a' is minimum response, 'b' is maximum response, 'c' is $IC_{50}$ and 'd' is Hill slope.

The results for individual compounds are provided below in Table 2 and are expressed as range of activity.

TABLE 2

| Example No. | h $P2X_3$ |
|---|---|
| 1 | ++ |
| 2 | ++ |
| 3 | +++ |
| 4 | ++ |
| 5 | +++ |
| 6 | ++ |
| 7 | +++ |
| 9 | ++ |
| 10 | ++ |
| 11 | ++ |
| 13 | +++ |
| 14 | ++ |
| 15 | ++ |
| 16 | ++ |
| 17 | ++ |
| 19 | ++ |

wherein the compounds are classified in term of potency with respect to their inhibitory activity on $P2X_3$ according to the following classification criterion:

+++: $pIC_{50}$ h $P2X_3$>6.5

++: 6.5<$pIC_{50}$ h $P2X_3$>5.5

In Vitro Electrophysiology Assay for $P2X_{2/3}$

Representative compound of the present invention have been also tested for $P2X_{2/3}$ receptor.

The same assay protocol was used for the $P2X_{2/3}$ assay as the $P2X_3$ assay with two modifications: 1) 10 μM ATP was used as the agonist; and 2) the mean current amplitude was measured seven seconds after the application of agonist.

The results of Table 3 indicate that representative compounds of the present invention are selective $P2X_3$ antagonist.

TABLE 3

| Example No. | h $P2X_3$ | h $P2X_{2/3}$ |
|---|---|---|
| 5 | +++ | ++ |
| 1 | ++ | + |

wherein the compounds are classified in term of potency with respect to their inhibitory activity on $P2X_3$ or $P2X_{2/3}$ isoforms according to the following classification criterion:

+++: $pIC_{50}$ h $P2X_3$ or h $P2X_{2/3}$>6.5

++: 6.5<$pIC_{50}$ h $P2X_3$ or h $P2X_{2/3}$>5.5

+: 5.5<$pIC_{50}$ h $P2X_3$ or h $P2X_{2/3}$>4.5.

Comparative Example A (7-(4-fluorophenyl)-N-((6-methylpyridazin-3-yl) methyl)isoquinolin-1-amine

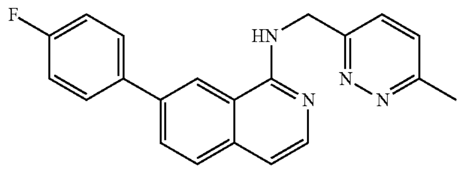 [SMILES: Cc1ccc(CNc2nccc3ccc(-c4ccc(F)cc4)cc23)nn1]

The activity of comparative Example A as has been tested in the in vitro assay for the determination of activity on $P2X_3$ receptor as described above.

Differently from the compounds of formula (I) of the present invention, the comparative Example A do not show a proper inhibitory activity on $P2X_3$, in fact the activity on receptor $P2X_3$ expressed as $pIC_{50}$ is <5.5.

The above results demonstrate that a proper position of the nitrogen atoms in the scaffold unexpectedly lead to a series of compounds that is active against the receptor $P2X_3$.

The invention claimed is:

1. A compound of formula (I)

(I)

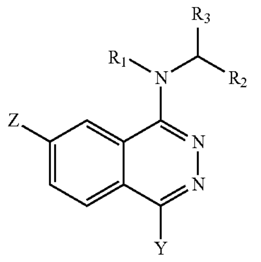

wherein

Z is selected from the group consisting of (5-6 membered)-heteroaryl and aryl, wherein any of such heteroaryl and aryl may be optionally substituted by one or more selected from the group consisting of (C1-C3) alkyl- and halo;

$R_1$ is H or (C1-C4) alkyl;

$R_2$ is selected from the group consisting of heteroaryl and ($C_3$-$C_8$) cycloalkyl-, wherein any of such heteroaryl may be optionally substituted by one or more selected from the group consisting of (C1-C3) alkyl, (C1-C6) haloalkyl and halo;

$R_3$ is H or (C1-C4) alkyl;

Y is selected from the group consisting of H, (C1-C4) alkyl-, (C3-C8) cycloalkyl-, (C3-C8) heterocycloalkyl, and (C3-C8) heterocycloalkyl-(C1-C4) alkyl-, or stereoisomer, tautomer, pharmaceutically acceptable salt, or solvate thereof.

2. The compound of formula (I), or stereoisomer, tautomer, pharmaceutically acceptable salt, or solvate thereof, according to claim 1, wherein the compound selected from the group consisting of:

N-((6-Methylpyridazin-3-yl) methyl)-7-(5-methylpyrimidin-2-yl)-4-(tetrahydro-2H-pyran-4-yl) phthalazin-1-amine, N-(Cyclopropylmethyl)-7-(4-fluorophenyl) phthalazin-1-amine, 7-(4-Fluorophenyl)-N-((6-methylpyridazin-3-yl) methyl) phthalazin-1-amine, (R)-4-Cyclopropyl-7-(4-fluorophenyl)-N-(1-(2-(trifluoromethyl) pyrimidin-5-yl) ethyl) phthalazin-1-amine, (R)-4-Cyclopropyl-7-(4-fluorophenyl)-N-(1-(6-methylpyridazin-3-yl) ethyl) phthalazin-1-amine, (R)-7-(4-Fluorophenyl)-4-(tetrahydro-2H-pyran-4-yl)-N-(1-(2-(trifluoromethyl) pyrimidin-5-yl) ethyl) phthalazin-1-amine, (R)-7-(4-Fluorophenyl)-N-(1-(6-methylpyridazin-3-yl) ethyl)-4-(tetrahydro-2H-pyran-4-yl) phthalazin-1-amine, 7-(5-Fluoropyridin-2-yl)-N-((6-methylpyridazin-3-yl) methyl)-4-(tetrahydro-2H-pyran-4-yl) phthalazin-1-amine, 7-(5-Fluoropyridin-2-yl)-N-((6-methylpyridazin-3-yl) methyl)-4-((tetrahydro-2H-pyran-4-yl) methyl) phthalazin-1-amine, 7-(5-Fluoropyridin-2-yl)-N-(1-(6-methylpyridazin-3-yl) ethyl)-4-(tetrahydro-2H-pyran-4-yl) phthalazin-1-amine, N-[(6-Methylpyridazin-3-yl) methyl]-7-(5-methylthiazol-2-yl) phthalazin-1-amine, 7-(5-Methylthiazol-2-yl)-4-((tetrahydro-2H-pyran-4-yl) methyl)-N-((3-(trifluoromethyl)-1,2,4-oxadiazol-5-yl) methyl) phthalazin-1-amine, N-((6-Methylpyridazin-3-yl) methyl)-7-(5-methylthiazol-2-yl)-4-((tetrahydro-2H-pyran-4-yl) methyl) phthalazin-1-amine, 7-(1-Methylpyrazol-3-yl)-N-[1-(6-methylpyridazin-3-yl) ethyl]-4-tetrahydropyran-4-yl-phthalazin-1-amine, and 4-Cyclopropyl-7-(1-methyl-1H-pyrazol-3-yl)-N-(1-(6-methylpyridazin-3-yl) ethyl) phthalazin-1-amine.

3. The compound of formula (I), or stereoisomer, tautomer, pharmaceutically acceptable salt, or solvate thereof, according to claim 1, wherein Y and $R_1$ are H, represented by the formula (Ia)

(Ia)

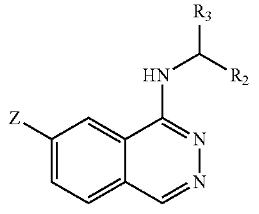

wherein

Z is selected from the group consisting of (5-6 membered)-heteroaryl and aryl, wherein any of such heteroaryl and aryl may be optionally substituted by one or more selected from the group consisting of ($C_1$-$C_3$) alkyl- and halo;

$R_2$ is selected from the group consisting of heteroaryl and ($C_3$-$C_8$) cycloalkyl-, wherein any of such heteroaryl may be optionally substituted by one or more ($C_1$-$C_3$) alkyl-;

$R_3$ is H or ($C_1$-$C_4$) alkyl.

4. A pharmaceutical composition comprising the compound or stereoisomer, tautomer, pharmaceutically acceptable salt, or solvate thereof, of claim 1, either alone or in combination with another one or more active ingredient, in admixture with one or more pharmaceutically acceptable carrier or excipient.

5. The pharmaceutical composition according to claim 4, formulated for oral administration.

6. A method of treating a disease involving one or more $P2X_3$ receptors, comprising administering to a subject in need thereof the pharmaceutical composition of claim 4, wherein the disease is a respiratory disease selected from the group consisting of cough, sub-acute cough, chronic cough, treatment-resistant cough, idiopathic chronic cough, post-viral cough, iatrogenic cough, asthma, idiopathic pulmonary fibrosis (IPF), chronic obstructive pulmonary disease (COPD) and bronchospasm.

7. The method of claim 6, wherein the disease is chronic cough.

8. The method according to claim 6, wherein the pharmaceutical composition is orally administered.

9. The method according to claim 7, wherein the pharmaceutical composition is orally administered.

* * * * *